United States Patent [19]

Itoh et al.

[11] Patent Number: 4,525,450
[45] Date of Patent: Jun. 25, 1985

[54] SILVER HALIDE COLOR PHOTOGRAPHIC LIGHT SENSITIVE MATERIAL CONTAINING A COUPLER CONTAINING AT LEAST ONE OF A SULFAMOYLPHENYLENESULFONYL, SULFAMOYLAMINOPHENYLENESULFONYL, OR SULFOAMIDOPHENYLENESULFONYL GROUP

[76] Inventors: Isamu Itoh; Takeshi Hirose, both of c/o Fuji Photo Film Co., Ltd. No. 210, Nakanuma, Minami Ashigara-shi, Kanagawa, Japan

[21] Appl. No.: 592,486

[22] Filed: Mar. 23, 1984

[30] Foreign Application Priority Data

Mar. 28, 1983 [JP] Japan ................. 58-52927

[51] Int. Cl.³ ............... G03C 7/00; G03C 7/32; G03C 1/40
[52] U.S. Cl. ............... 430/552; 430/553; 430/554; 430/555; 430/556; 430/557; 430/558; 430/565
[58] Field of Search ............. 430/552, 553, 554, 555, 430/556, 557, 558, 565

[56] References Cited

U.S. PATENT DOCUMENTS

| | | | |
|---|---|---|---|
| 4,362,810 | 12/1982 | Usagawa et al. | 430/553 X |
| 4,390,606 | 6/1983 | Gabrielsen et al. | 430/357 X |
| 4,433,050 | 2/1984 | Abe et al. | 430/552 X |
| 4,443,536 | 4/1984 | Lestina | 430/557 X |

FOREIGN PATENT DOCUMENTS 651958 4/1951 United Kingdom ............. 430/552
1160628 8/1969 United Kingdom ............. 430/556

OTHER PUBLICATIONS

C.A. 101: 46203a–Konishiroku Phot., vol. 101, 1984.
C.A. 100: 212166s, Konishiroku Phot., vol. 100, 1984.
C.A. 99: 131398c, Fuji Photo, vol. 99, 1983.

*Primary Examiner*—John E. Kittle
*Assistant Examiner*—Mukund J. Shah

[57] ABSTRACT

A silver halide color photographic light-sensitive material containing a coupler having at least one of a sulfamoylphenylenesulfonyl group, a sulfamoylaminophenylenesulfonyl group and a sulfonamidophenylenesulfonyl group as a substituent. Preferred couplers are represented by the formula:

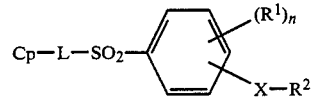

wherein all moieties are defined in the specification wherein Cp is a coupler residue, L is a divalent linking group and X represents $-NHSO_2-$,

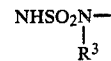

or $-SO_2NH$, and n represents 0-4. Groups $R^1$, $R^2$ and $R^3$ are defined in the specification.

7 Claims, No Drawings

SILVER HALIDE COLOR PHOTOGRAPHIC LIGHT SENSITIVE MATERIAL CONTAINING A COUPLER CONTAINING AT LEAST ONE OF A SULFAMOYLPHENYLENESULFONYL, SULFAMOYLAMINOPHENYLENESULFONYL, OR SULFOAMIDOPHENYLENESULFONYL GROUP

FIELD OF THE INVENTION

The present invention relates to color photographic light-sensitive materials containing novel couplers.

BACKGROUND OF THE INVENTION

In order to form color photographic images by a subtractive process, a process of forming cyan, magenta and yellow dye images which comprises reducing silver halide grains in exposed or chemically fogged emulsions with a developing agent such as an aromatic primary amine compound, particularly, a N,N-disubstituted p-phenylene-diamine compound, to cause reactions of couplers with a simultaneously formed oxidation product of the developing agent is generally utilized.

Couplers used for the above described color developing process are compounds having a phenolic hydroxyl group, an anilinic amino group, an active methylene group or an active methine group which form a dye by oxidative coupling with an aromatic primary amine developing agent.

Suitable couplers which form a cyan dye by reacting with an oxidation product of the color developing agent are phenols and naphthols. Exemplary forming a magenta dye are pyrazolones, pyrazolotriazoles, pyrazolobenzimidazolones, imidazolones, cyanoacetophenones and diaminoaniline, etc. Couplers forming a yellow dye include α-amylacetamides, β-ketoacetic acid esters and N,N-malondiamides, etc.

In order to add couplers as described above to photographic emulsion layers, various methods have been proposed. However, it is preferred to use a method of adding couplers which comprises dissolving couplers with a ballast group in the coupler in an organic solvent, and dispersing the solution by emulsification. Characteristics required for such couplers having a ballast group in order to produce color light-sensitive materials having excellent photographic properties are as follows. Namely, (1) Couplers and developed dyes formed by color development have high solubility in high boiling point organic solvents (for example, tricresyl phosphate) used for dispersing the couplers.
(2) Silver halide photographic emulsions having dispersed therein the couplers have high stability and when the emulsions are applied to a support and dried, stable coating films are obtained.
(3) They have an excellent antidiffusion property and do not diffuse into other layers.
(4) They have an excellent dyeing property, and dyed color images have an excellent spectral absorption characteristic. Further, they have good color and density stabilities and high fastness to light.
(5) They can be obtained in good purity and high yield from inexpensive raw materials by a simple synthetic process.

Hitherto, many attempts of modifying the structure of a ballast group have been made in order to improve the above described characteristics. Examples of these attempts have been described in Japanese Patent Publication Nos. 5582/67, 5391/71 and 27563/64, U.S. Pat. Nos. 2,589,004 and 2,908,573, Japanese Patent Publication No. 3660/69, U.S. Pat. Nos. 2,474,293, 2,039,970 and 2,920,961, Japanese Patent Publication No. 36078/71, U.S. Pat. No. 2,589,004, British Pat. No. 944,838, Japanese Patent Publication No. 19026/71, U.S. Pat. No. 2,659,329, British Pat. No. 1,813,832, Japanese Patent Application (OPI) No. 76834/78, Japanese Patent Publication No. 36856/79, Japanese Patent Application (OPI) No. 76834/78, Japanese Patent Publication No. 36856/79, Japanese Patent Application (OPI) No. 82411/78, German Patent Application (OLS) No. 2,707,488, and Japanese Patent Application (OPI) Nos. 139534/78, 141622/78, 23528/79, 48541/79, 65035/79, 99433/79 and 121126/79, etc.

However, couplers having a ballast group known hitherto have some disadvantages and they do not satisfy the above described characteristics which are required for them. Many of these couplers with an oleophilic ballast group have excellent stability and antidiffusibility in emulsion layers, spectral absorption characteristics of color images, durability of color images and aptitude for synthesis as compared with other types of couplers (for example, couplers having an acid group which are added to emulsion layers as a micellar aqueous solution). However, those which have a satisfactory color forming property have not yet been found. In rapid processing at high temperature which has been used actively in recent years, the color forming property is particularly important, and insufficient color formation becomes a serious problem. In order to compensate for this insufficient color formation, depending on the circumstances addition of an organic solvent such as benzyl alcohol as a color forming accelerator to the developing solution has been employed. However, organic solvents for accelerating color formation have some disadvantages. For example, (1) Since they are absorbed in the emulsion layers in the development step, the amount thereof in the developing solution is reduced with deterioration of color formation occurring.
(2) They are carried into the bleaching solution or the blixing solution with obstruction of desilvering or deterioration of dye densities occurring.
(3) They remain in the light-sensitive materials after processing, deteriorating the fastness of color images.
(4) They are admixed with waste liquors causing an increase of B.O.D. and C.O.D. in the waste liquors.

Therefore, it has been highly desired to remove or reduce the amount of organic solvents for accelerating color formation.

In couplers containing a ballast group having a p-hydroxyphenylenesulfonyl group or a p-hydroxyphenylenesulfinyl group at the terminal of the group as described in European Patent Publication (Unexamined) No. 73636, improvement of the color forming property is observed as compared with prior couplers, but even so the degree of improvement is not sufficient. Further, they have the disadvantage of having low solubility in organic solvents for dispersing couplers.

SUMMARY OF THE INVENTION

A first object of the present invention is to provide couplers suitable for color photographic light-sensitive materials having excellent photographic properties.

A second object of the present invention is to provide color photographic light-sensitive materials having silver halide emulsions which contain couplers having a novel substituent.

A third object of the present invention is to provide color photographic light-sensitive materials using couplers having a novel substituent by which a sufficient color forming property is obtained even if organic solvents for accelerating color formation, such as benzyl alcohol, etc., are not present in the color developing solution or are present in reduced amount.

A fourth object of the present invention is to provide color photographic light-sensitive materials suitable for rapid processing at high temperature, wherein novel couplers are used.

It has now been found that the above described objects are attained by providing silver halide color photographic light-sensitive materials containing at least one coupler having at least one of a sulfamoylphenylenesulfonyl group, a sulfamoylaminophenylenesulfonyl group and a sulfonamidophenylenesulfonyl group.

DETAILED DESCRIPTION OF THE INVENTION

The coupling group in couplers used in color photographic light-sensitive materials of the present invention may be any coupling group which is known in this art to form a colored or colorless coupling product upon reaction with the oxidation product of a developing agent, and the sulfamoylphenylenesulfonyl group, the sulfamoylaminophenylenesulfonyl group or the sulfonamidophenylenesulfonyl group may be attached at any position of the coupling group. Two or more of the above described groups may be attached to one coupling group.

Preferred couplers used in the present invention are represented by the general formula (I):

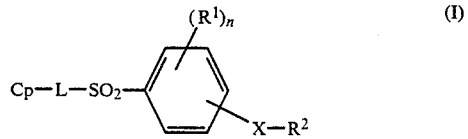

In the general formula (I), Cp represents a coupler residue; L represents a linking group; X represents $-NHSO_2-$,

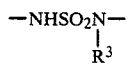

or $-SO_2NH-$; $R^1$, $R^2$ and $R^3$ each represents a substituent; and n represents 0-4.

Suitable cyan coupler residues for Cp include phenols and naphthols, exemplary magenta coupler residues for Cp include pyrazolones, pyrazolotriazoles, pyrazolobenzimidazoles, imidazolones, cyanoacetophenones and 4-aminoanilines, and suitable yellow coupler residues for Cp are α-acylacetamides, β-ketoacetic acid esters, β-diketones and N,N-malondiamides, etc. Further, in addition to these residues, as coupler residues forming a black or gray dye by reacting with an oxidation product of the developing agent, resorcinols and 3-aminophenols, etc., can be used. Further, coupler residues forming a colorless compound by reacting with an oxidation product of the color developing agent include indanones, etc. The coupler residues may have substituents other than hydrogen atoms at the coupling positions reactive with an oxidation product of the color developing agent (coupling positions), and the coupling positions may be substituted by a group having a sulfamoylphenylenesulfonyl group, a sulfamoylaminophenylenesulfonyl group or a sulfonamidophenylenesulfonyl group as a substituent. Further, Cp may be substituted by two or more of the above described ballast groups.

The divalent linking group represented by L may be any group conventionally used in this art. For example, alkylene groups having 1 to 10 carbon atoms, arylene groups having 6 to 16 carbon atoms, aralkylene groups having 7 to 17 carbon atoms, heterocyclic groups having 5 to 10 carbon atoms, an oxygen atom, a sulfur atom, amino groups, carbonamido groups, sulfonamido groups, carbamoyl groups, sulfamoyl groups, ureido groups, sulfamoylamino groups, carbamoyloxy groups, oxycarbonamido groups, acyl groups, alkoxycarbonyl groups, a carboxyl group, a sulfone group and combinations of these linking groups, for example, aminoalkylene groups, aminoarylene groups, amidoarylene groups, amidoalkylene groups, oxyalkylene groups, oxyarylene groups, thioalkyleneamino groups, aminoalkylamino groups, aminoarylamino groups, carbamoylarylamino groups, sulfamoylarylamino groups, carbamoylalkylamino groups, sulfamoylalkylamino groups, ureidoarylamino groups, amidoarylamino groups, aminoaryloxy groups, aminoalkyloxy groups, carbamoylaryloxy groups, sulfamoylaryloxy groups, amidoaryloxy groups and sulfamoylaryl groups, etc., can be employed.

$R^1$ represents a substituent on the benzene ring. Typical examples for $R^1$ are an alkyl group, an aryl group, an alkoxy group, a hydroxyl group, an acyl group, a carboxyl group, a sulfo group, a carbonamido group, a cyano group or a nitro group, etc. n is 0-4.

$R^2$ represents an alkyl group, an aryl group or an alkoxy group, which may be a hydrogen atom or a hydroxyl group where X is $-NHSO_2NR^3-$ or $-SO_2NH-$.

$R^3$ represents a substituent on the nitrogen atom, and can be a hydrogen atom, an alkyl group, an aryl group, an alkoxy group, a hydroxyl group or a heterocyclic residue. Also, $R^2$ and $R^3$ may combine and form a ring.

Preferred couplers which can be used in the present invention are represented by the following general formula (II):

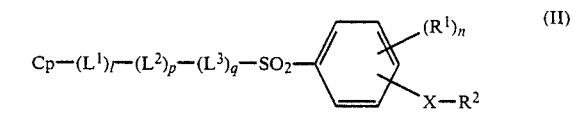

wherein the general formula (II), Cp, $R^1$, $R^2$, X and n have each the same meaning as in the general formula (I), and l, p and q each is 0 or 1, $L^1$ represents a divalent group selected from groups of the formula

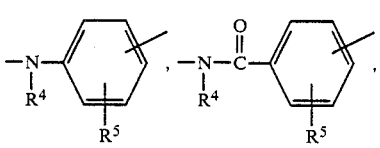

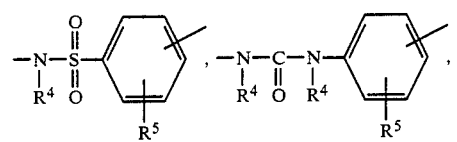

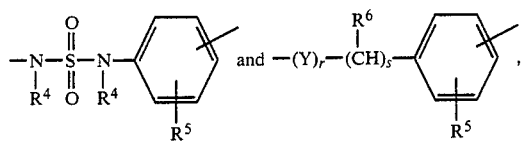

L² represents a divalent group selected from groups of the formula

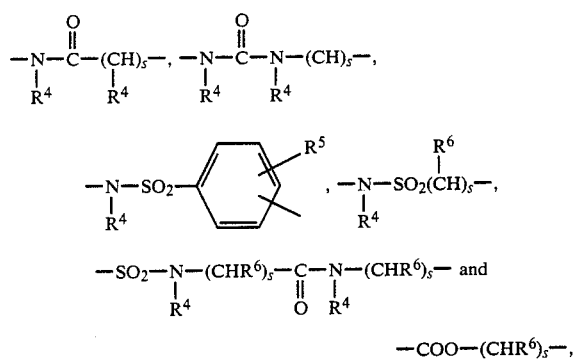

L³ represents a divalent group selected from groups of the formula

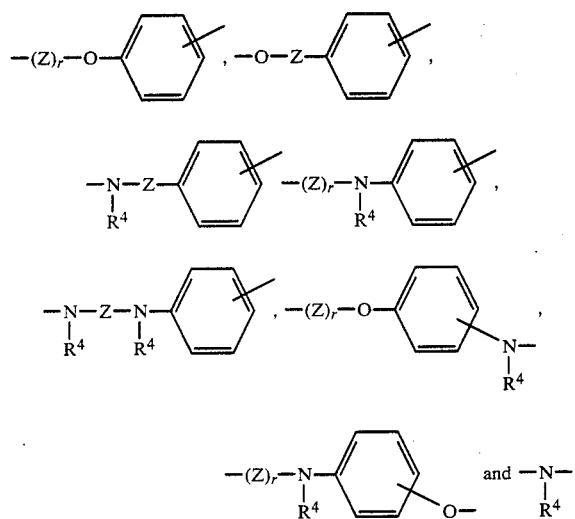

$R^4$ and $R^6$ represent each a hydrogen atom, an alkyl group or an aryl group, $R^5$ represents a hydrogen atom, a halogen atom, an alkyl group, an alkoxy group, a sulfamoyl group, a sulfamoylamino group, a carbonamido group, carbamoyl group, a sulfonamido group, an acyl group, a ureido group, a carboxyl group, an acyl group, a carbamate group, a cyano group or a nitro group, etc., Y represents —O— or —S—, Z represents —CO— or —SO₂—, r is 0 or 1, and s is 0 to 10.

Particularly preferred couplers which can be used in the present invention are represented by the following general formulas (III) and (IV):

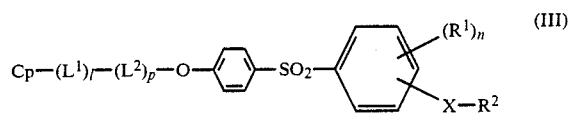

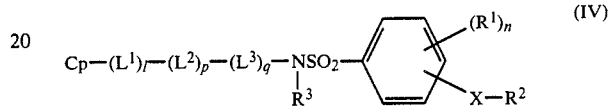

In the general formulas (III) and (IV), Cp, $L^1$, $L^2$, $L^3$, $R^1$, $R^2$, $R^3$, X, l, p, q and n each have the same meaning as in the general formula (II).

In the general formulas (III) and (IV), where X represents —SO₂NH—, X preferably is in the meta-position to the —SO₂— group bonded to the substituent containing the Cp residue. Where X represents —NH—SO₂— or —NHSO₂NR³—, X is preferably is in the meta-position or para-position, and preferably a para-position to the —SO₂— group bonded to the substituent containing the Cp residue.

n is 0 to 4, preferably 0 to 2, and more preferably 0 to 1.

$R^1$ is preferably an alkyl group having 1 to 8 carbon atoms, an alkoxy group or a halogen atom and, more preferably is a methyl group, an ethyl group, a methoxy group or a chlorine atom.

$R^2$ is preferably a hydrogen atom, an alkyl group having 1 to 16 carbon atoms, or an aryl group having 6 to 20 carbon atoms and, more preferably, is an alkyl group having 1 to 8 carbon atoms or an aryl group having 6 to 10 carbon atoms.

$R^3$ is preferably a hydrogen atom or an alkyl group having 1 to 5 carbon atoms and, more preferably, is a hydrogen atom, a methyl group or an ethyl group.

Couplers represented by the general formula (I) used in the present invention are described below, but the present invention is not to be construed to be limited to these couplers.

Yellow Couplers:

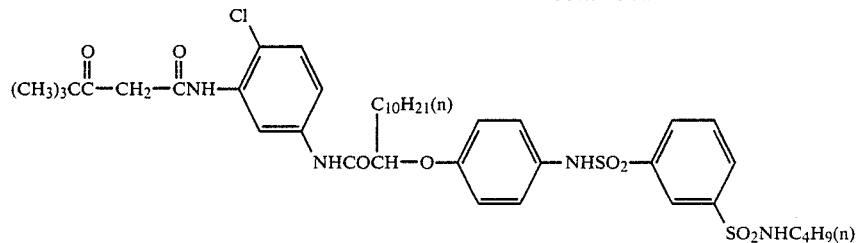
Y-1
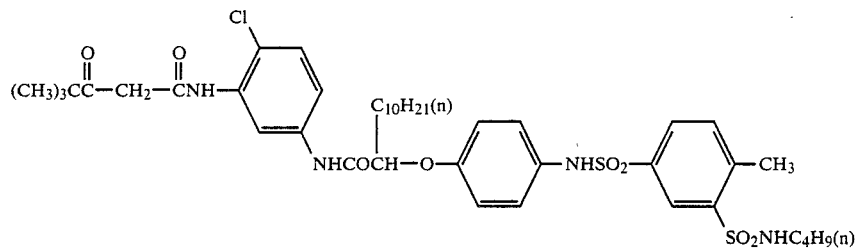
Y-2
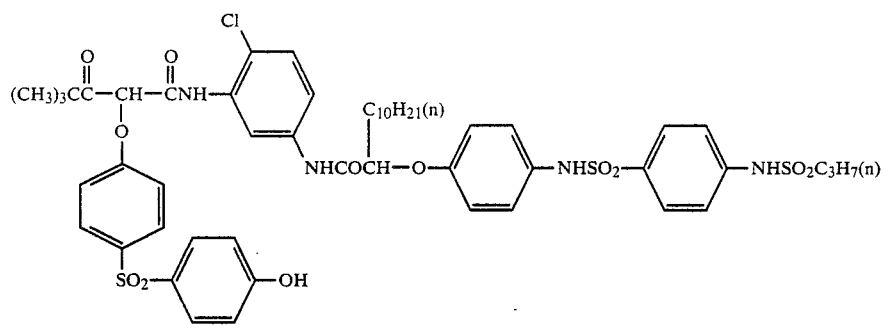
Y-3
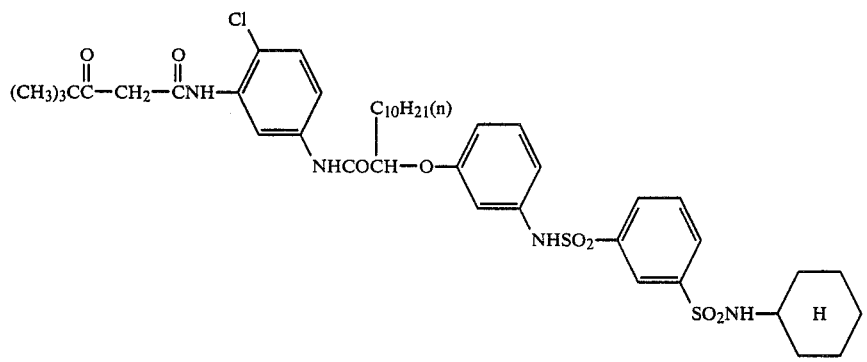
Y-4
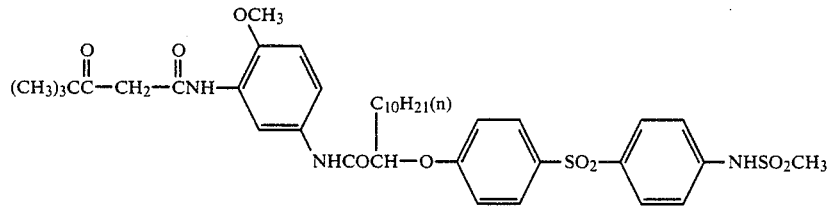
Y-5
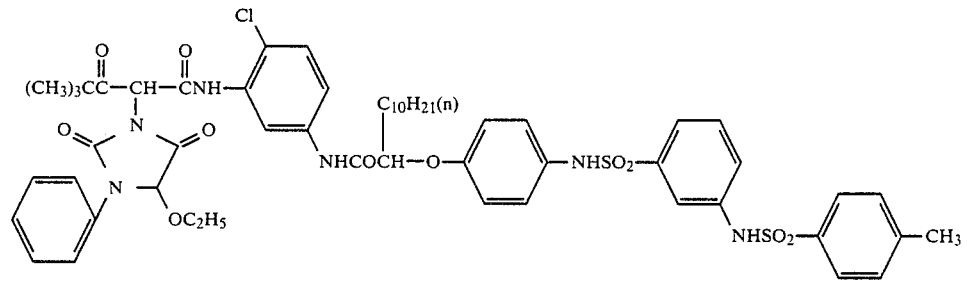
Y-6

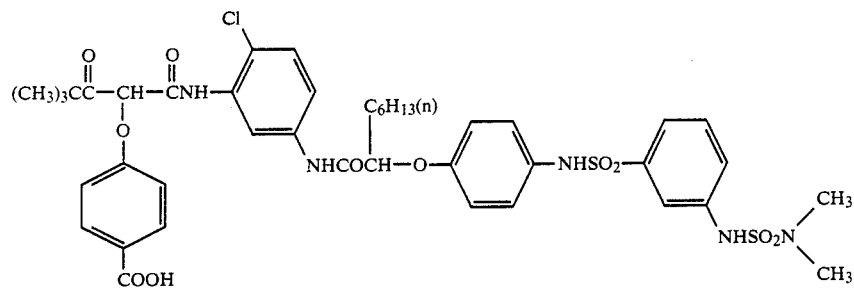
Y-7
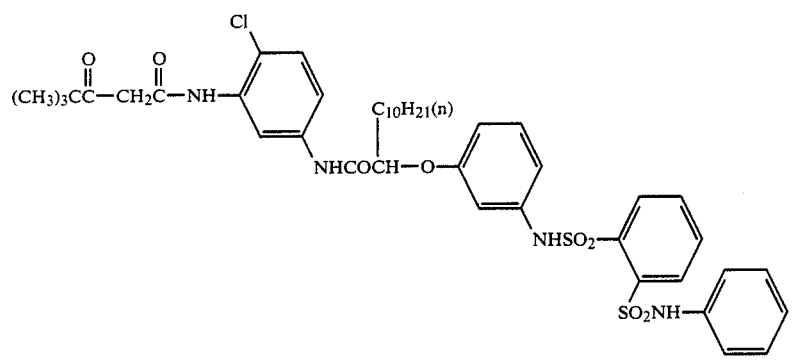
Y-8
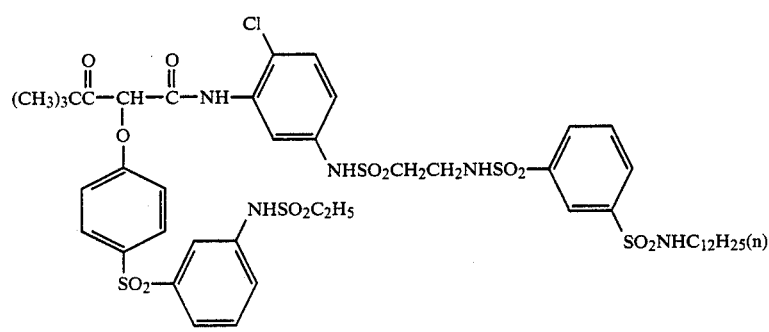
Y-9
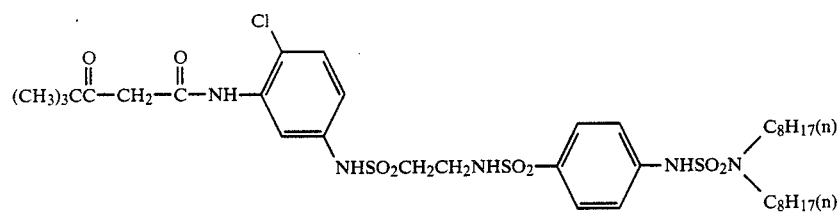
Y-10
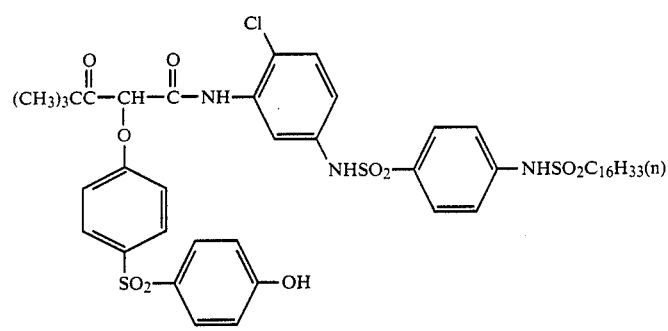
Y-11

-continued
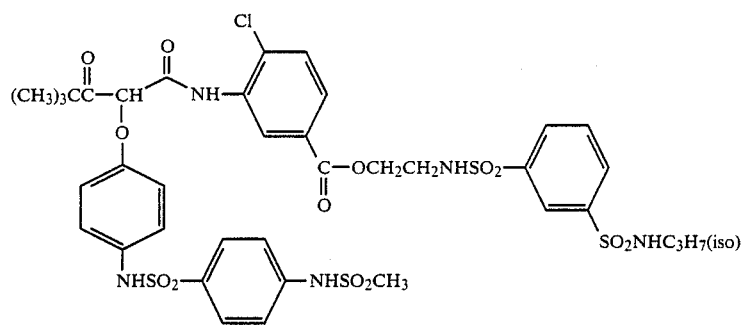
Y-12
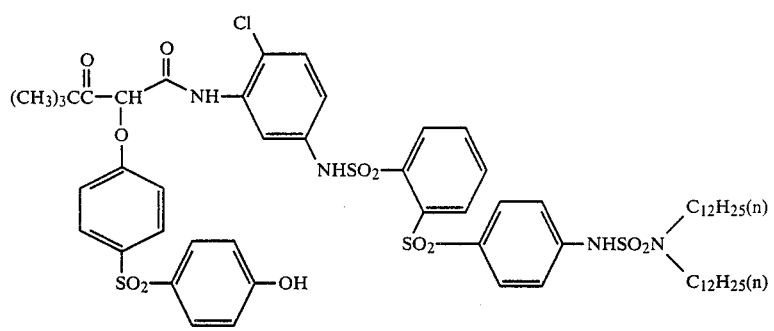
Y-13
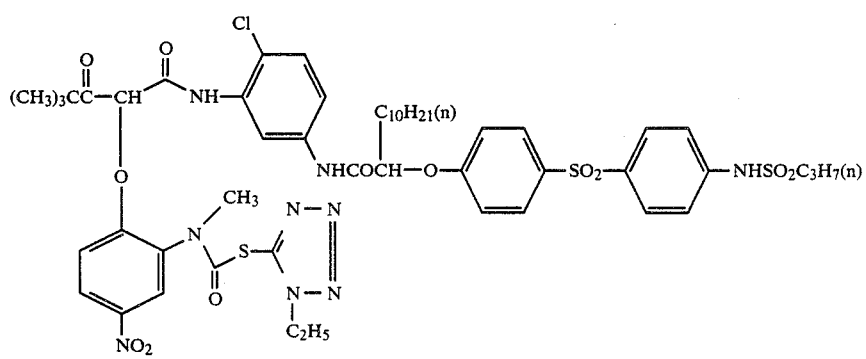
Y-14
Magenta Couplers:
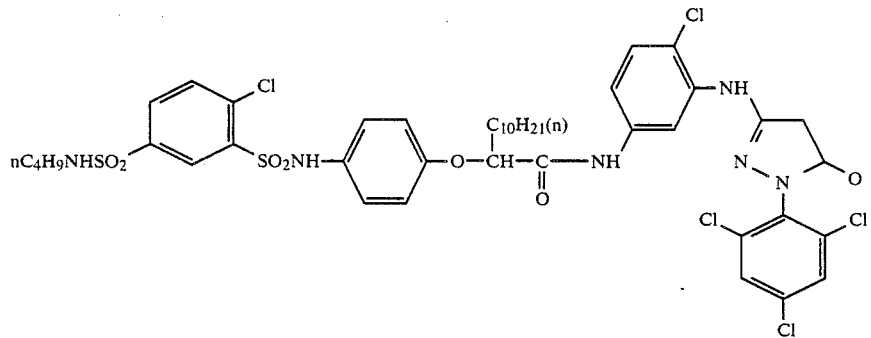
M-1

-continued
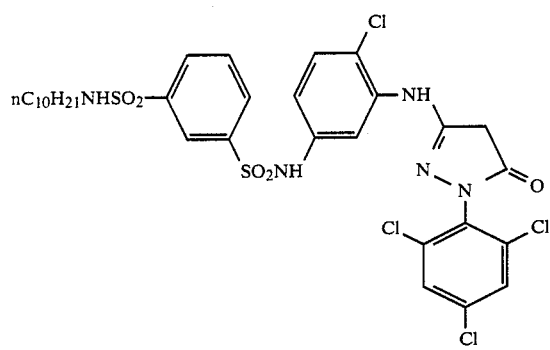
M-2
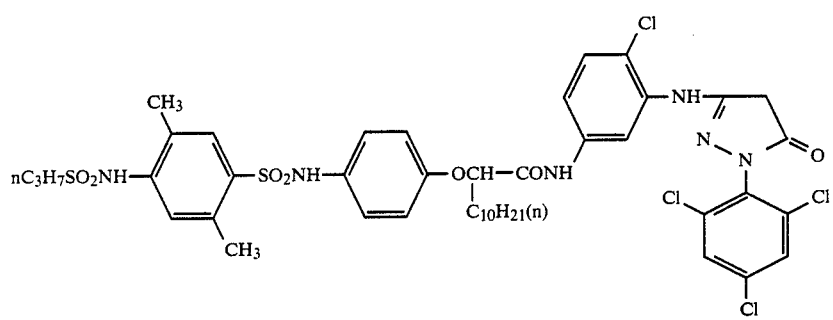
M-3
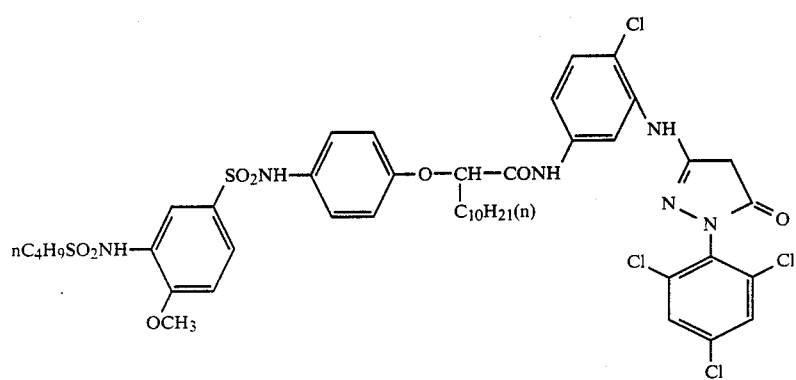
M-4
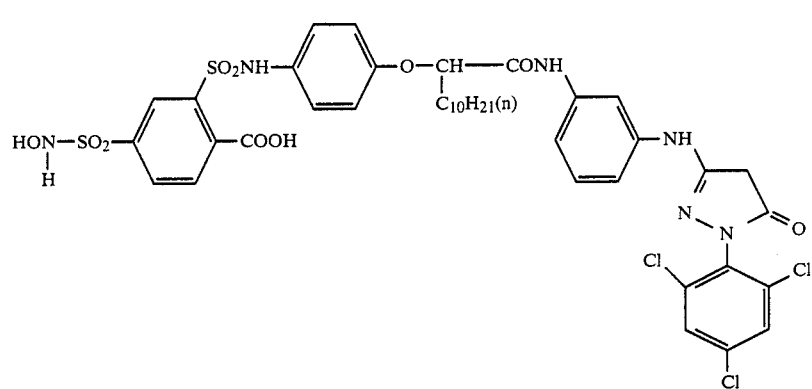
M-5

-continued
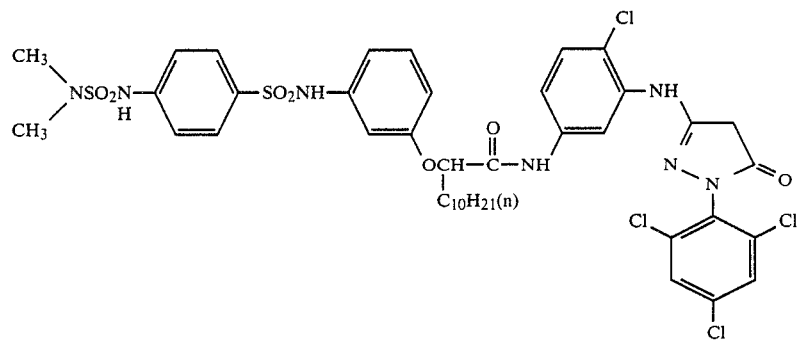
M-6
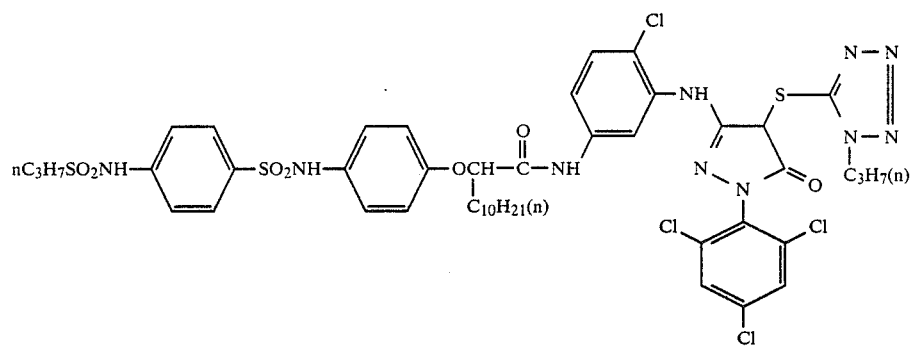
M-7
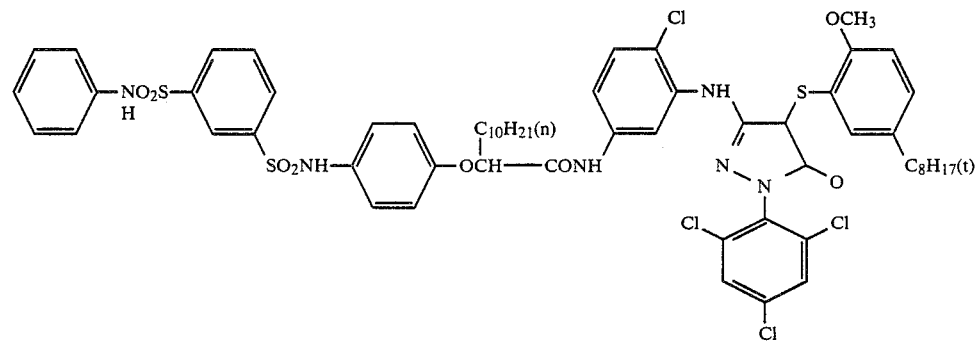
M-8
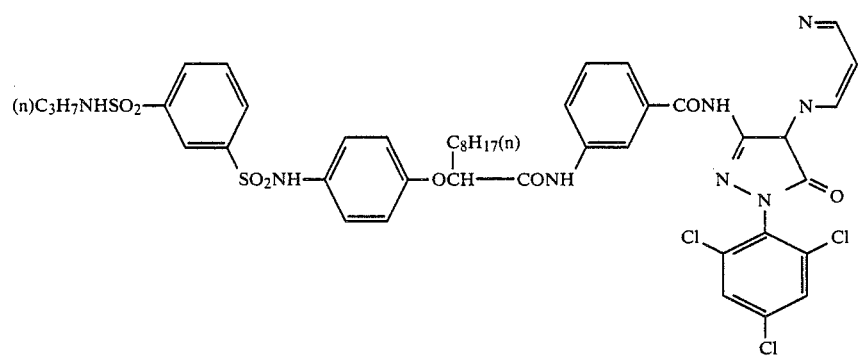
M-9

-continued
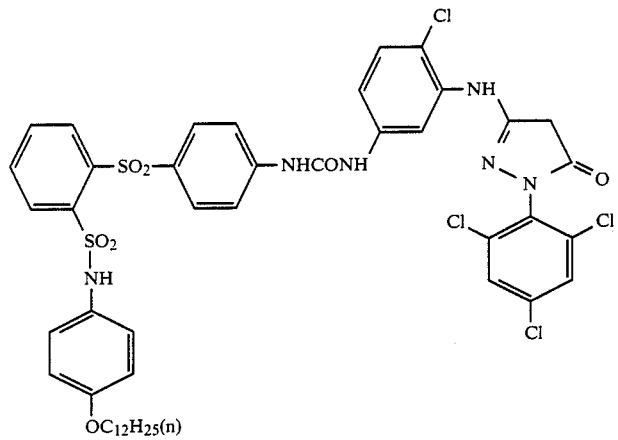
M-10
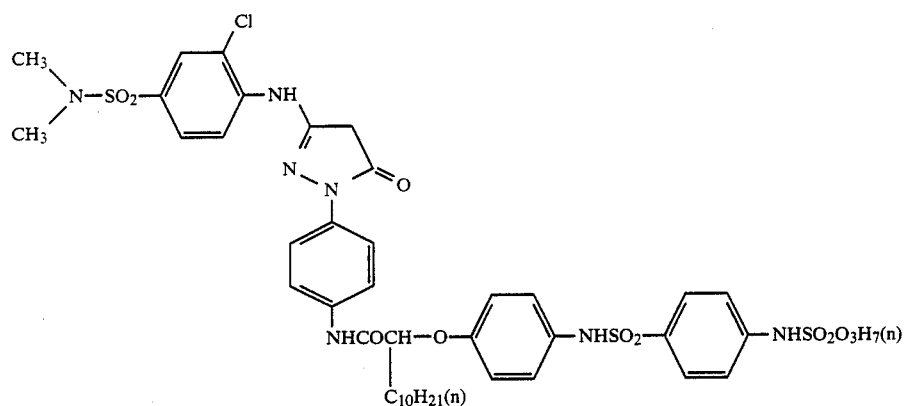
M-11
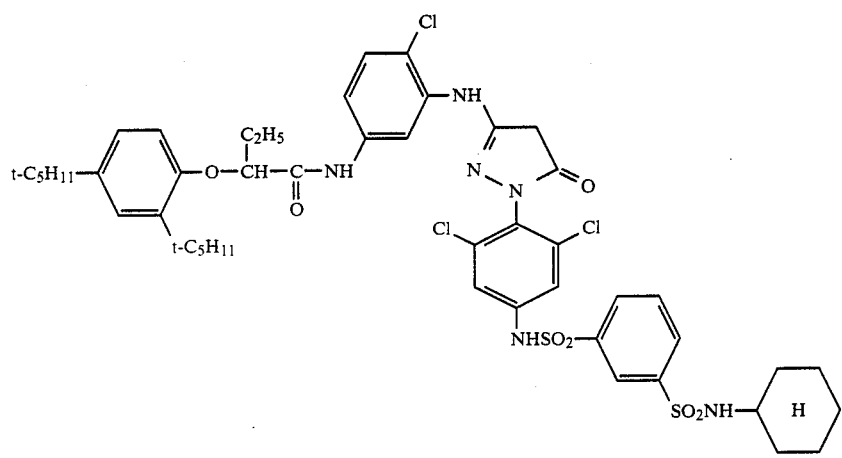
M-12
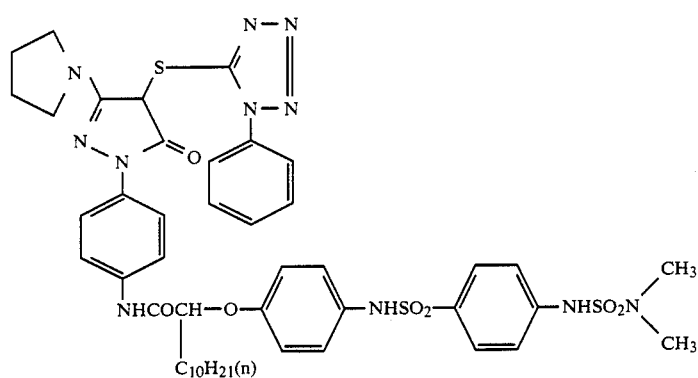
M-13

-continued
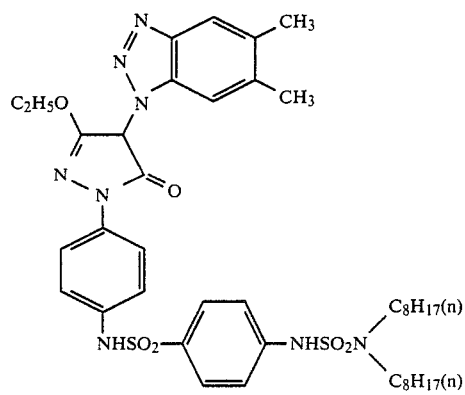
M-14
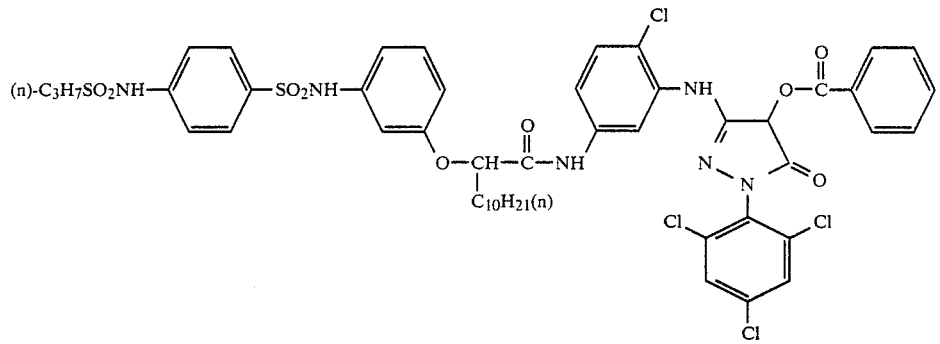
M-15
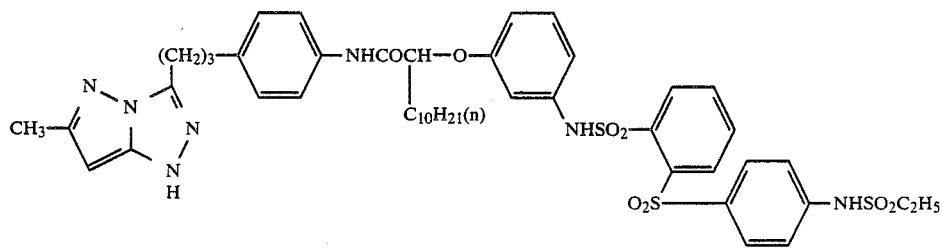
M-16
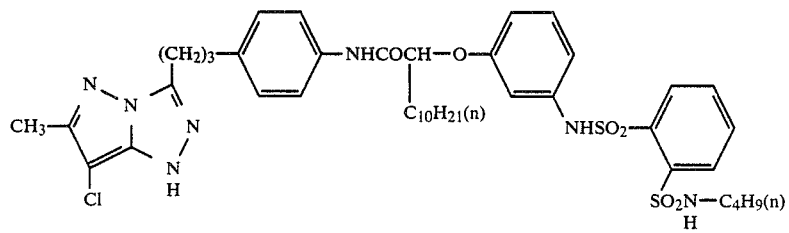
M-17
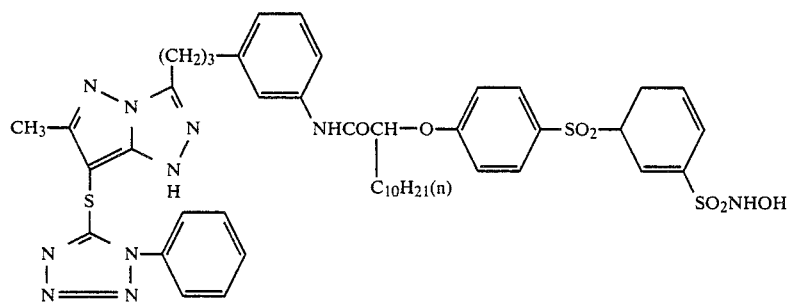
M-18

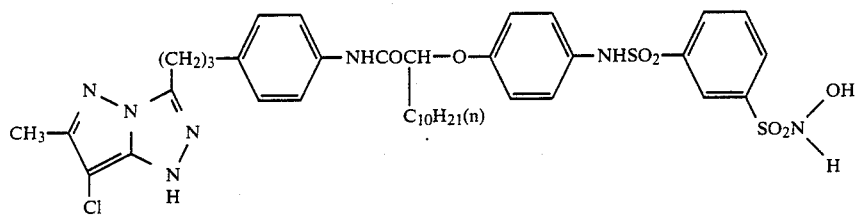
M-19
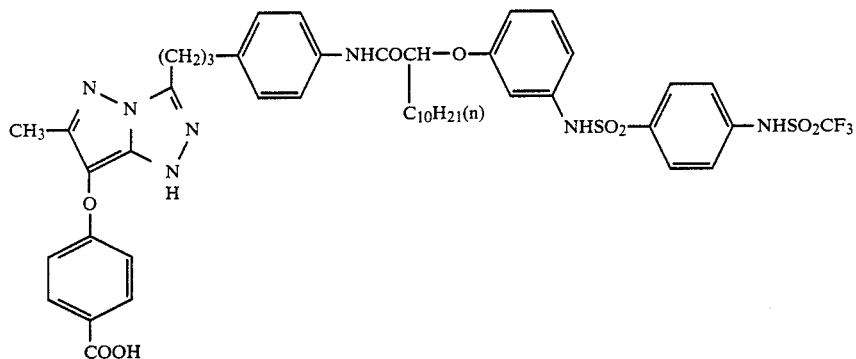
M-20
Cyan Couplers:
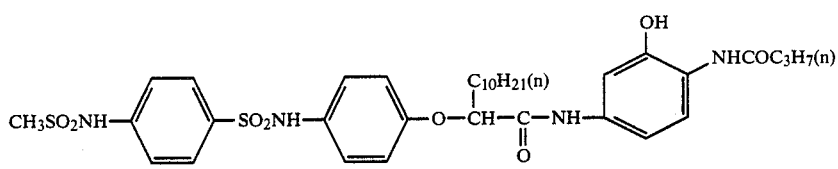
C-1
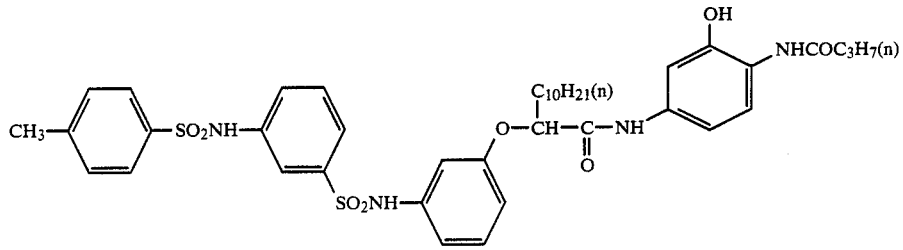
C-2
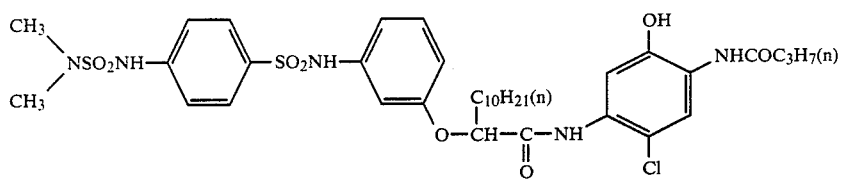
C-3
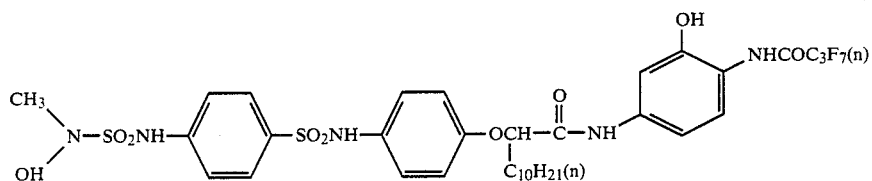
C-4
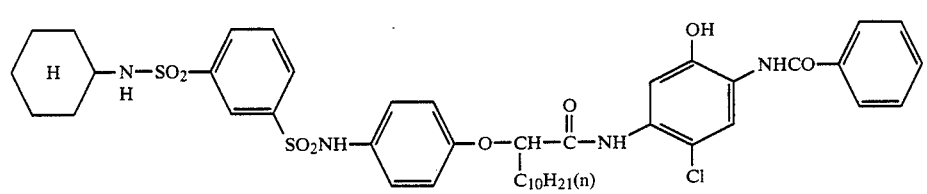
C-5

-continued
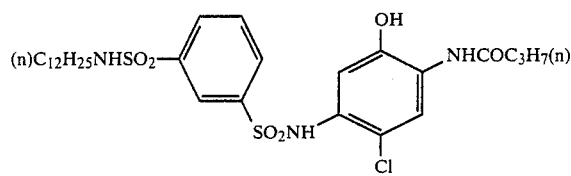
C-6
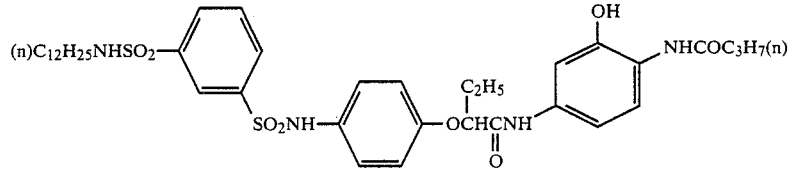
C-7
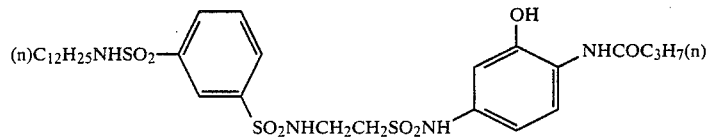
C-8
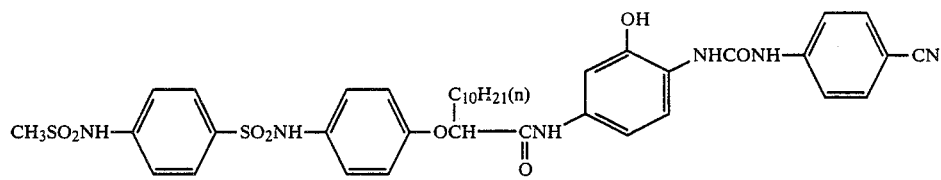
C-9
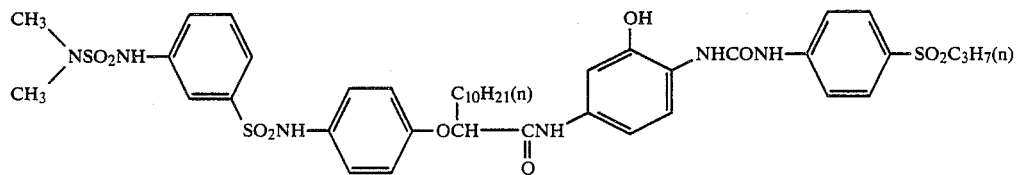
C-10
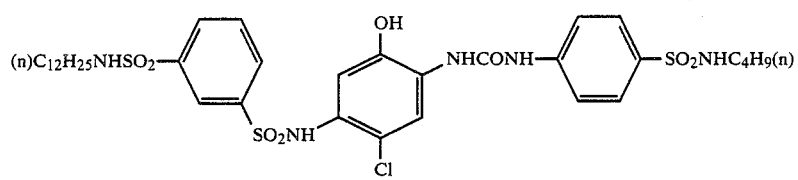
C-11
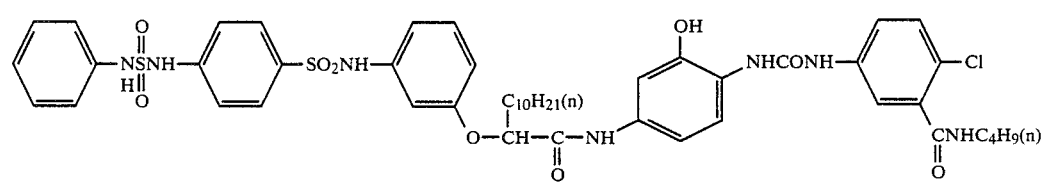
C-12
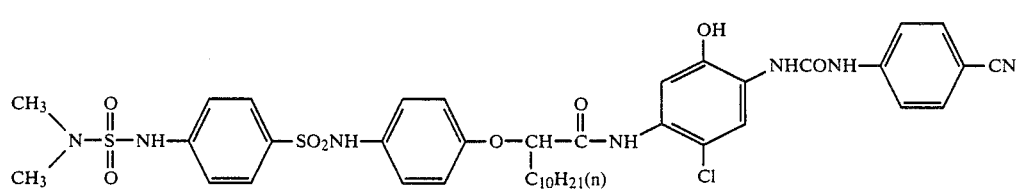
C-13

-continued
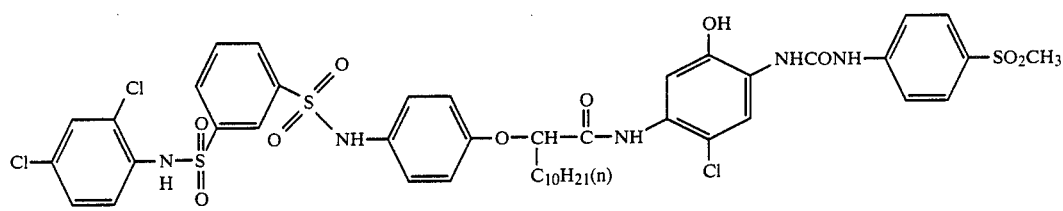
C-14
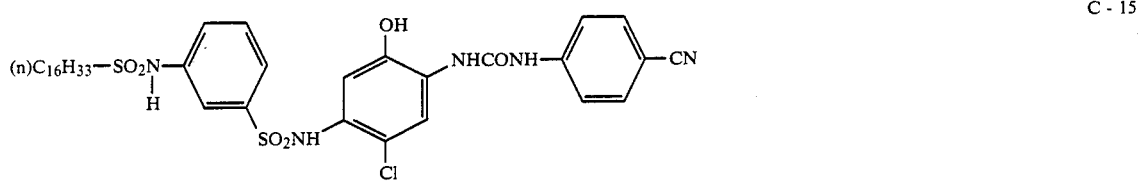
C-15
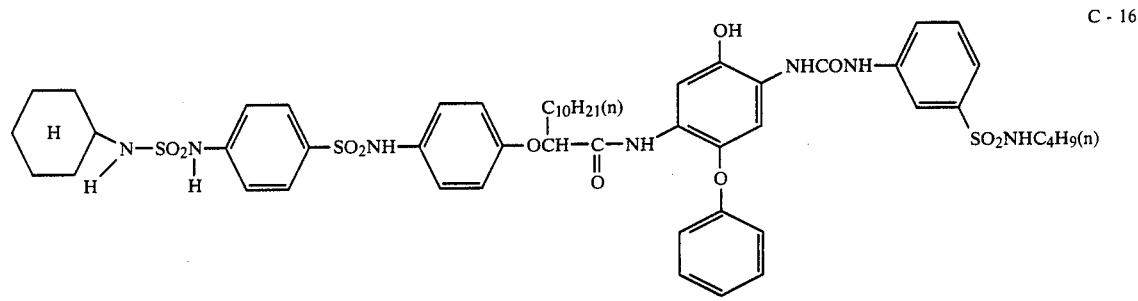
C-16
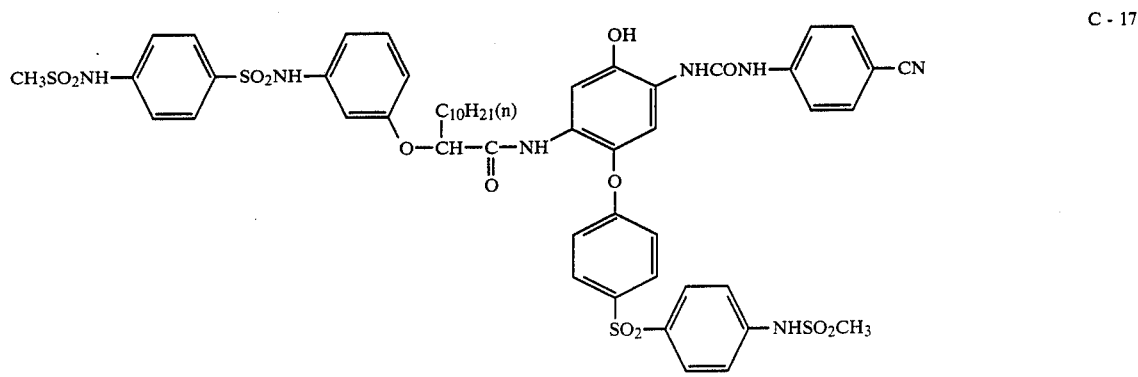
C-17
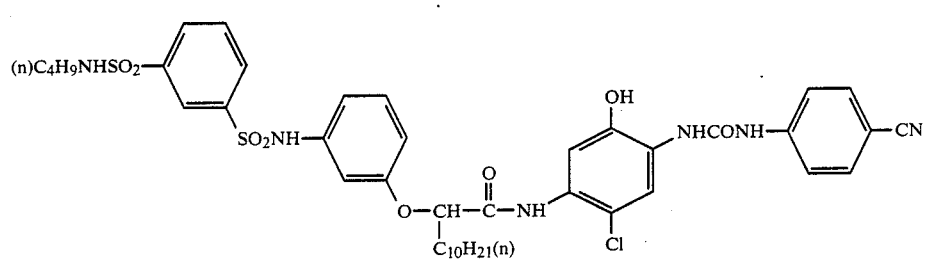
C-18
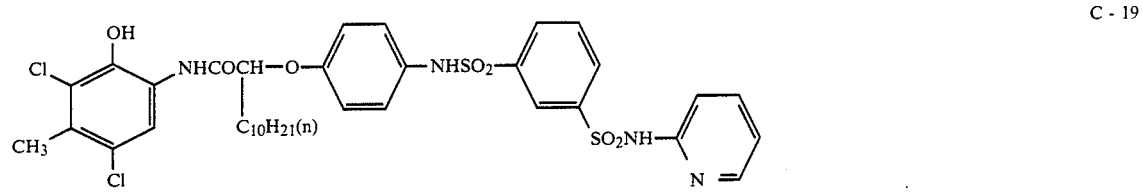
C-19

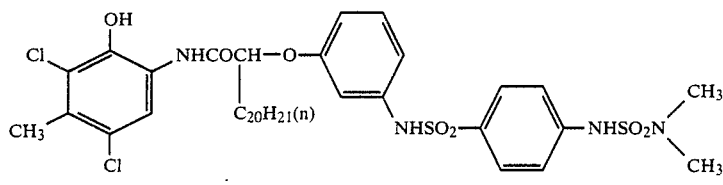

C-20

Colorless Coupler:

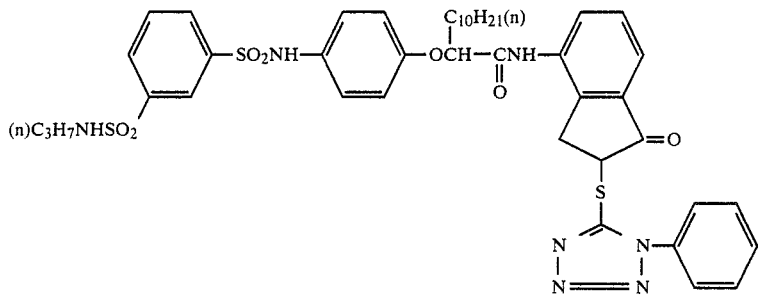

W-1

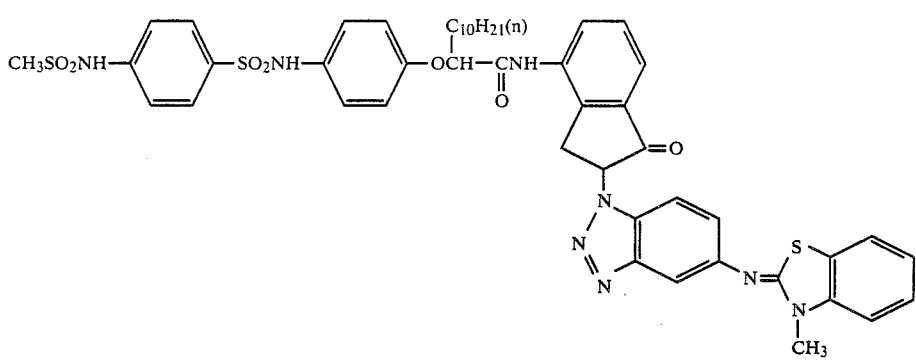

W-2

The couplers used in the present invention can be synthesized, for example, as follows.

Where X in the general formula (I) represents a sulfamoyl group, an amine compound is selectively reacted with disulfonyl chloride to obtain the sulfamoylsulfonyl chloride, but it is not suitable for obtaining selectively a mono-substituted product, because a large excess amount of disulfonyl chloride should be used. A process by which the above described disadvantage is removed involves utilizing m-benzenesulfonyl chloride sulfonyl fluoride described in Japanese Patent Application (OPI) No. 126331/74. This process can be utilized similarly for producing compounds with other substituents. Since sulfonyl chloride is highly reactive as compared with sulfonyl chloride, selective sulfonamidation of sulfonyl chloride first proceeds and thereafter the second sulfonamidation can be carried out by increasing the reaction temperature with adding the second amine compound or by adding an amine compound having high reactivity.

Scheme 1

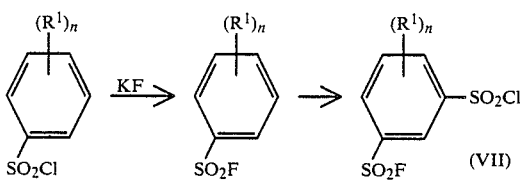

-continued
Scheme 1

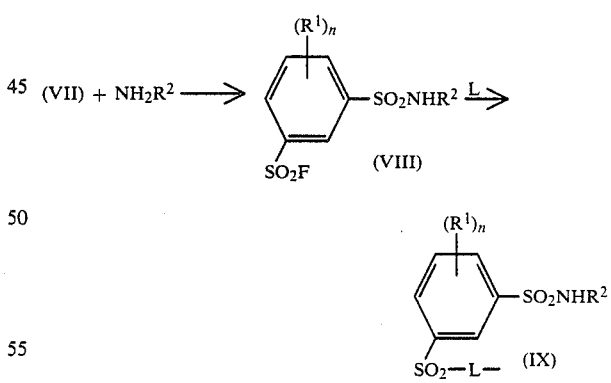

Conversion of sulfonyl chloride into sulfonylfluoride is described in detail in *Journal of Organic Chemistry*, vol. 28, page 3426, (1963). (IX) can be synthesized by a reaction of inserting —SO$_2$Cl— into a diazonium salt, too. This process is described in detail in E. E. Gilbert; *Synthesis*, 1969, vol. 1–10, page 6.

Where X is a sulfonamido group or a sulfamoylamino group, the synthesis can be carried out using aminobenzenesulfonic acid as the raw material.

Examples of the synthesis of couplers used in the present invention are described below. Unless other-

SYNTHESIS EXAMPLE 1

Synthesis of Coupler Y-1

Synthesis of 4-(3-n-Butylsulfamoylbenzenesulfonamido)-phenol

A solution of 1,3-benzenesulfonylchloride sulfonyl fluoride (25.9 g, 0.1 mol) in tetrahydrofuran (100 ml) was cooled to about 5° C. To the solution, n-butylamine (7.3 g, 0.1 mol) was added dropwise. After about 10 minutes, triethylamine (10.1 g, 0.1 mol) was added dropwise, and the mixture was stirred at about 5° C. for 1 hour. Then, p-aminophenol (10.9 g, 0.1 mol) and pyridine (7.9 g, 0.1 mol) were added to the reaction mixture, and the mixture was stirred at room temperature (about 20°–30° C.) for 2 hours and further at 50° C. for 30 minutes. The reaction solution was poured into an aqueous solution of 1N hydrochloric acid cooled to about 5° C., and extraction was carried out with ethyl acetate (100 ml, two times). After the extracted solution was dried with Glauber's salt, it was concentrated under reduced pressure to obtain 28 g of a crude oily product of the desired compound.

Synthesis of 2-(4-(3-n-Butylsulfamoylbenzenesulfonamido)phenoxy)dodecanoyl Chloride To a solution of methy 2-bromododecanoate (14.5 g, 0.05 mol) and the above described phenol (19.2 g, 0.05 mol) in acetone (200 ml), potassium carbonate (34.5 g, 0.25 mol) was added, and the solution was refluxed with heating on an oil bath for 16 hours under a nitrogen atmosphere. The solids were filtered out with heating, and the filtrate was concentrated to obtain an oily product of the phenoxyester compound. The oily product was added without purifying to acetonitrile (200 ml), and an aqueous solution (50 ml) of potassium hydroxide (3 g, 0.055 mol) was added dropwise thereto. After stirring was continued at room temperature for about 4 hours, the mixture was poured into ice water and the pH was adjusted to about 4 with hydrochloric acid. The crystals separated were filtered off, washed with cold methanol and dried. The resulting carboxylic acid was added to thionyl chloride (100 ml), and the mixture was refluxed with heating for about 1 hour. Excess thionyl chloride was distilled away under a reduced pressure to obtain 16.5 g of crude crystals of the desired compound.

Synthesis of Coupler Y-1

To a solution containing α-pivalyl-2-chloro-5-aminoacetanilide (5.4 g, 0.02 mol) and pyridine (1.8 ml) in acetonitrile (40 ml), a solution of the above described acid chloride (12 g, 0.02 mol) in acetonitrile (30 ml) was added dropwise at about 5° C. After stirring at room temperature for 1 hour, the reaction solution was slowly poured into ice water (100 ml). The solidified crystals were filtered off to obtain a crude product of Coupler Y-1. The crude product was recrystallized from a solvent mixture of chloroform/n-hexane (70:30 by vol) to obtain 12.3 g of white crystals of Coupler Y-1.

SYNTHESIS EXAMPLE 2

Synthesis of Coupler M-3

Synthesis of 2,5-Dimethyl-4-n-propylsulfonamidobenzenesulfonyl Chloride 2,5-Dimethylsulfanilic acid (20.1 g, 0.1 mol) and pyridine (8.7 g, 0.11 mol) were added to tetrahydrofuran (200 ml), and n-propylsulfonyl chloride (14.3 g, 0.1 mol) was added dropwise to the resulting solution at about 5° C. with cooling. After the reaction was carried out at 5° C. for about 30 minutes and then at room temperature for about 1 hour, tetrahydrofuran was distilled away under a reduced pressure. After the residue was washed with a cold sodium chloride solution, it was dried under a reduced pressure to obtain a crude product of the desired sulfonic acid. This crude product was dissolved in acetonitrile (250 ml), and excess phosphorus oxychloride (23.6 g, 0.2 mol) was added thereto, and the mixture was refluxed with heating for 1 hour. The reaction solution was poured into ice water and the crystals separated were filtered off to obtain 28 g of the desired compound.

Synthesis of 4-(2,5-Dimethyl-4-n-propylsulfonamido)phenol

The above described sulfonyl chloride (16.3 g, 0.05 mol) and p-aminophenol (5.5 g, 0.05 mol) were added to dimethylacetamide (100 ml) at about 5° C., and pyridine (4.2 g, 0.053 mol) was added dropwise thereto. After stirring at room temperature for 1 hour, the reaction solution was poured into ice water and crystals separated were filtered off to obtain 17 g of the desired compound.

Synthesis of Coupler M-3

Using 0.02 mols of the above described 4-(2,5-dimethyl-4-n-propylsulfonamido)phenyl and 0.02 mols of methyl 2-bromododecanoic acid as raw materials, phenoxylation, hydrolysis of the methyl ester and acid chlorination by thionyl chloride were carried out using the same procedure as in Synthesis Example 1 for Coupler Y-1 to obtain about 8.2 g of 2-[4-(2,5-dimethyl-4-n-propylsulfonamido)phenol]dodecanoyl chloride (6.8 g, 0.01 mol). The resulting acid chloride (6.9 g, 0.01 mol) was condensed with an equimolar amount of 3-(5-amino-2-chloroanilino)-1-(2,4,6-trichlorophenyl)-5-pyrazolone (4.0 g) in a presence of pyridine (0.011 mol) to obtain about 9.2 g of crude crystals. By purification using silica gel chromatography, 5.8 g of the desired coupler was obtained.

SYNTHESIS EXAMPLE 3

Synthesis of Coupler C-8

Synthesis of 2-(3-n-Dodecylsulfamoylbenzenesulfonamido)ethanesulfonyl chloride 1,3-Benzenesulfonyl chloride sulfonyl fluoride (13 g, 0.05 mol) was dissolved in tetrahydrofuran (60 ml), and n-dodecylamine (9.3 g, 0.05 mol) and triethylamine (5.1 g, 0.05 mol) were added dropwise thereto at about 5° C. After stirring for 30 minutes, the reaction temperature was increased to room temperature, and further, taurine (6.3 g, 0.05 mol) and triethylamine (5.1 g, 0.05 mol) were added dropwise thereto. After the reaction had been continued at room temperature for about 5 hours, the reaction solution was poured into a cold aqueous solution of 1N hydrochloric acid. The crystals separated were dissolved in ethyl acetate. After drying, the solvent was distilled away under a reduced pressure to obtain about 17.6 g of the sulfonic acid. It was added to acetone (200 ml) and the mixture was refluxed with phosphorus oxychloride (10 g) with heating. To the reaction solution, chloroform (200 ml) was added. After cooling to room temperature, it was washed with water and dried ($Na_2SO_4$). The solvent was distilled away to obtain 15.7 g of the desired compound.

Synthesis of Coupler C-8

A solution containing 5-amino-2-n-butyramidophenol (3.9 g, 0.02 mol) and pyridine (1.7 g, 0.022 mol) in dimethylacetamide (20 ml) was cooled with ice to about 5° C., and a solution of ethanesulfonyl chloride (10.6 g, 0.02 mol) in tetrahydrofuran (40 ml) was added dropwise to the above described solution. The mixture was stirred for about 30 minutes and the temperature was increased to room temperature. The reaction solution was poured into a cold aqueous solution of 1N hydrochloric acid and the crystals separated were filtered off. By recrystallization from ethyl acetate/n-hexane (70:30 by vol), 6.8 g of the desired coupler was obtained.

The amount of the couplers in the present invention is not restricted, but it is generally 5 to 1500 g and preferably 10 to 500 g per mol of silver halide in the emulsion.

The present invention is illustrated in greater detail by reference to the examples given below. Again, unless otherwise indicated, all parts, percents, ratios and the like are by weight.

EXAMPLE 1

10 g of Coupler C-1 of the present invention was dissolved in a mixture of 5 ml of dibutyl phthalate and 10 ml of ethyl acetate, and the resulting solution was blended with 100 ml of a 10% aqueous solution of gelatin containing 0.1 g of sodium dodecylbenzenesulfonate and stirred at 50° C. using a homogenizer revolving at a high rate to obtain a coupler emulsified dispersion. This dispersion was blended with 150 g of a silver chlorobromide (Cl/Br: 30/70 by mol) emulsion, and 15 ml of a 2% aqueous solution of 2-hydroxy-4,6-dichloro-s-triazine Na salt and 6 ml of a 5% aqueous solution of saponin were added thereto. The mixture was applied to a cellulose acetate film so as to result in a silver amount of 1 $g/m^2$, and a gelatin protective layer having a dry film thickness of 1μ was applied to the resulting layer to produce Sample A. Samples B-R were produced in the same manner as Sample A as shown in Table 1 below, except that the molar amount of the coupler applied and the amount of silver applied were adjusted so as to be equal to those in Sample A. In Samples D, E, F, J, K, L, P, Q and R, comparative couplers were used.

After Samples A-R were exposed stepwise to light for sensitometry, they were subjected to the following development processing.

| Process | Temperature | Time |
| --- | --- | --- |
| Color Development | 38° C. | 3 minutes |
| Water Wash | " | 1 minute |
| Bleach-Fixation | " | 1 minute and 30 seconds |
| Water Wash | " | 1 minute |

The composition of the color developing solutions was as follows.

| | CD-1 | CD-2 | CD-3 |
| --- | --- | --- | --- |
| Benzyl Alcohol | — | — | 15 ml |
| Diethylene Glycol | — | — | 8 ml |
| Developing Agent | 4-Amino-3-methyl-N—ethyl-N—β-hydroxyethyl-aniline sulfate | 4-Amino-3-methyl-N—ethyl-N—β-(methanesulfon-amido)ethylanil-ine sulfate | Same as CD-2 |
| | 3.5 g | 5 g | 5 g |
| Sodium Sulfite | 2 g | 2 g | 2 g |
| Hydroxylamine Sulfate | 3 g | 3 g | 3 g |
| Potassium Carbonate | 30 g | 30 g | 30 g |
| Water to make | 1 | 1 | 1 |
| pH (adjusted) | 10.2 | 10.2 | 10.2 |

The composition of the bleach-fixing solution was as follows.

| Disodium Ethylenediaminetetraacetate | 2 g |
| --- | --- |
| Ethylenediaminetetraacetic Acid Ferric Salt | 40 g |
| Sodium Sulfite | 5 g |
| Ammonium Thiosulfate | 70 g |
| Water to make | 1 |
| pH was adjusted to 6.8. | |

The comparative couplers used for comparison were as follows:

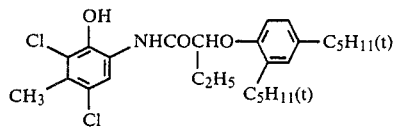

CR-1

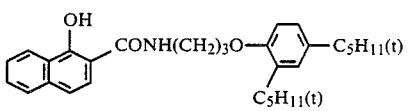

CR-2

-continued

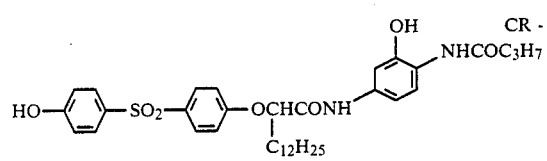 CR-3

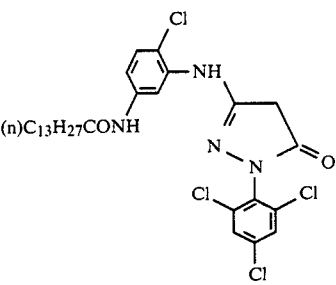 MR-1

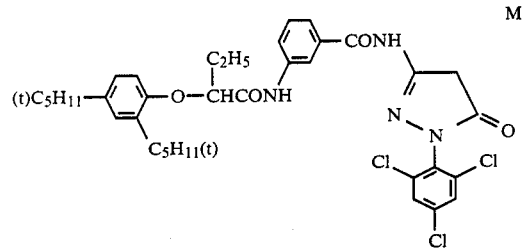 MR-2

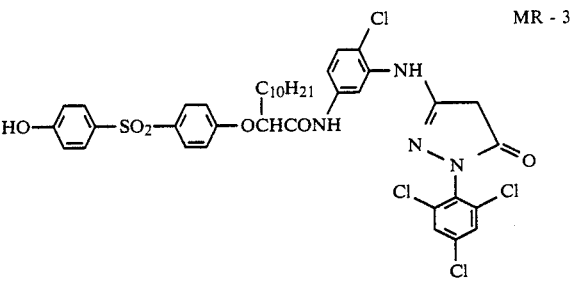 MR-3

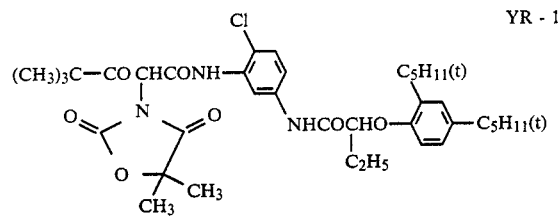 YR-1

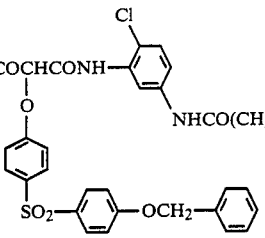 YR-2

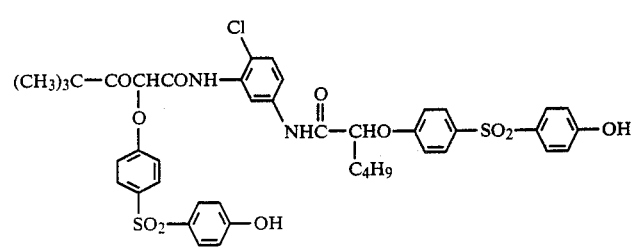 YR-3

Transmitted light densities of the each resulting sample were measured (cyan, magenta or yellow density was measured according to each dye) and the maximum densities and γ were determined. The results obtained are shown in Table 1 below.

TABLE 1

| Sample | Coupler | CD-1 Dmax | CD-1 γ | CD-2 Dmax | CD-2 γ | CD-3 Dmax | CD-3 γ |
|---|---|---|---|---|---|---|---|
| A | C-1 | 3.45 | 2.48 | 3.40 | 2.39 | 3.43 | 2.42 |
| B | C-8 | 3.39 | 2.45 | 3.35 | 2.38 | 3.37 | 2.40 |
| C | C-17 | 3.48 | 2.51 | 3.42 | 2.42 | 3.46 | 2.45 |
| D | CR-1 | 2.80 | 1.88 | 2.23 | 1.43 | 2.78 | 1.90 |
| E | CR-2 | 2.65 | 1.52 | 2.01 | 1.22 | 2.72 | 1.58 |
| F | CR-3 | 3.01 | 2.00 | 2.83 | 1.91 | 3.12 | 2.12 |
| G | M-2 | 3.51 | 2.51 | 3.46 | 2.47 | 3.48 | 2.49 |
| H | M-3 | 3.62 | 2.53 | 3.56 | 2.49 | 3.58 | 2.51 |
| I | M-17 | 3.41 | 2.48 | 3.35 | 2.42 | 3.38 | 2.45 |
| J | MR-1 | 2.93 | 2.03 | 2.78 | 1.92 | 3.16 | 2.12 |
| K | MR-2 | 3.03 | 2.09 | 2.88 | 1.95 | 3.09 | 2.10 |
| L | MR-3 | 3.15 | 2.17 | 3.06 | 2.03 | 3.21 | 2.15 |
| M | Y-1 | 3.39 | 2.46 | 3.34 | 2.41 | 3.36 | 2.44 |
| N | Y-3 | 3.45 | 2.49 | 3.39 | 2.43 | 3.41 | 2.45 |
| O | Y-9 | 3.48 | 2.50 | 3.41 | 2.42 | 3.45 | 2.45 |
| P | YR-1 | 3.01 | 1.98 | 2.64 | 1.57 | 2.99 | 1.95 |
| Q | YR-2 | 2.80 | 1.43 | 2.15 | 1.21 | 2.79 | 1.55 |
| R | YR-3 | 3.05 | 2.03 | 2.90 | 1.84 | 3.08 | 2.05 |

It can be seen from these results that good color formation is exhibited in Samples A, B, C, G, H, I, M, N and O containing couplers of the present invention, even if processed with any color developing solution, whereas Dmax or γ is low and color formation is poor in Comparative Samples D, E, F, J, K, L, P, Q and R. Particularly, it can be seen by comparison CD-2 and CD-3 which contain the same comparatively active color developing agent, that Comparative Samples undergo serious deterioration of color formation in the case of processing with CD-2 which does not contain benzyl alcohol, while the Samples of the present invention show only a small difference between the case of using CD-2 and the case of using CD-3 and sufficient color formation can be carried out without using benzyl alcohol.

EXAMPLE 2

To a laminated paper, both sides of which were covered with polyethylene, a first layer (the lowest layer)–a sixth layer (the top layer) were applied as shown in Table 2 below to produce color photographic light-sensitive materials, Samples A–C.

The coating solution for the first layer was prepared as follows. Namely, 10 g of yellow coupler shown in Table 2 was dissolved in a mixture of 166.7 ml of dibutyl phthalate (DBP) and 200 ml of ethyl acetate, and the resulting solution was dispersed by emulsification in 800 g of a 10% aqueous solution of gelatin containing 80 ml of a 1% aqueous solution of sodium dodecylbenzene sulfonate, and the resulting emulsified dispersion was then blended with 1450 g (containing 66.7 g of Ag) of a blue-sensitive silver chlorobromide emulsion (Br 80 mol %) to prepare a coating solution. Coating solutions for the other layers were prepared in the same manner. 2,4-Dichloro-6-hydroxy-s-triazine sodium salt was used as a hardening agent for each layer.

The following substances were used as spectral sensitizers for each emulsion.

Blue-Sensitive Emulsion Layer: 3,3'-Di-($\gamma$-sulfopropyl)selenacyanine sodium salt ($2 \times 10^{-4}$ mols per mol of silver halide)

Green-Sensitive Emulsion Layer: 3,3'-Di-($\gamma$-sulfopropyl)-5,5'-diphenyl-9-ethyloxacarbocyanine sodium salt ($2.5 \times 10^{-4}$ mols per mol of silver halide)

Red-Sensitive Emulsion Layer: 3,3'-Di-($\gamma$-sulfopropyl)-9-methyl-thiadicarbocyanine sodium salt ($2.5 \times 10^{-4}$ mols per mol of silver halide)

The following dyes were used as anti-irradiation dyes in each emulsion layer.

Green-Sensitive Emulsion Layer:

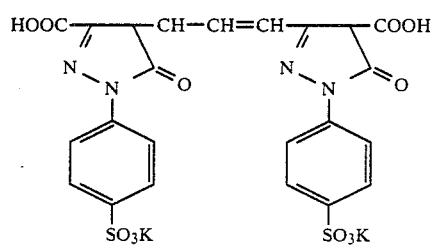

Red-Sensitive Emulsion Layer:

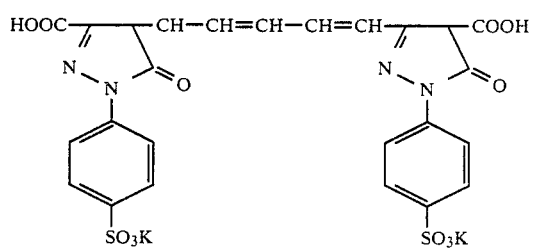

The chemical structure of solvents in Table 2 above is as follows.

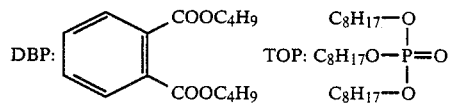

TABLE 2

|  |  | Sample No. | | |
|---|---|---|---|---|
|  |  | A | B | C |
| Sixth Layer (Protective layer) | Amount of Gelatin Applied | 1500 mg/m² | " | " |
| Fifth Layer (Red-sensitive layer) | Silver Chlorobromide Emulsion (Br: 50 mol %) |  |  |  |
|  | Amount of Ag | 300 mg/m² | " | " |
|  | Cyan Coupler | CR-1 | C-1 | C-17 |
|  | Amount applied | 400 mg/m² | 580 mg/m² | 670 mg/m² |
|  | Solvent | DBP | " | " |
|  | Amount of solvent applied | 240 mg/m² | 350 mg/m² | 400 mg/m² |
| Fourth Layer (Ultraviolet ray absorbing layer) | Amount of Gelatin Applied | 2000 mg/m² | " | " |
|  | Ultraviolet Ray Absorbing Agent Amount applied | UV-1 15 mg/m² | " | " |
|  |  | UV-2 45 mg/m² | " | " |
|  |  | UV-3 90 mg/m² | " | " |
|  | Solvent | DBP | " | " |
|  | Amount of solvent applied | 60 mg/m² | " | " |
| Third Layer (Green-sensitive layer) | Silver Chlorobromide Emulsion (Br: 70 mol %) |  |  |  |
|  | Amount of Ag | 450 mg/m² | " | " |
|  | Magenta Coupler | MR-1 | M-3 | M-8 |
|  | Amount applied | 350 mg/m² | 560 mg/m² | 700 mg/m² |
|  | Solvent | TOP | " | " |
|  | Amount of solvent applied | 440 mg/m² | 700 mg/m² | 880 mg/m² |
| Second Layer (Intermediate layer) | Amount of Gelatin Applied | 1500 mg/m² | " | " |
| First Layer (Blue-sensitive layer) | Silver Chlorobromide Emulsion (Br: 80 mol %) |  |  |  |
|  | Amount of Ag | 1500 mg/m² | " | " |

TABLE 2-continued

| | | Sample No. | | |
|---|---|---|---|---|
| | | A | B | C |
| | Yellow Coupler | YR-1 | Y-9 | Y-3 |
| | Amount applied | 600 mg/m$^2$ | 870 mg/m$^2$ | 910 mg/m$^2$ |
| | Solvent | DBP | " | " |
| | Amount of solvent applied | 1000 mg/m$^2$ | 1400 mg/m$^2$ | 1500 mg/m$^2$ |
| Support | | Laminated paper support, both sides of which were covered with polyethylene | | |

After each sample was exposed stepwise to light for sensitometry, development processing was carried out in the same manner as in Example 1. However, CD-2 and -3 were used as color developing solutions. The reflection densities (red, green and blue densities) of the resulting processed samples were measured and fog, Dmax and γ were determined. The results obtained are shown in Table 3 below.

TABLE 3

| | Cyan | | | Magenta | | | Yellow | | |
|---|---|---|---|---|---|---|---|---|---|
| Sample | Fog | γ | Dmax | Fog | γ | Dmax | Fog | γ | Dmax |
| | | | | CD-2 | | | | | |
| A | 0.08 | 2.78 | 2.12 | 0.07 | 2.82 | 2.23 | 0.09 | 2.84 | 2.14 |
| B | 0.12 | 3.21 | 2.62 | 0.09 | 3.42 | 2.78 | 0.13 | 3.29 | 2.85 |
| C | 0.12 | 3.21 | 2.61 | 0.11 | 3.42 | 2.79 | 0.13 | 3.30 | 2.90 |
| | | | | CD-3 | | | | | |
| A | 0.10 | 3.23 | 2.58 | 0.08 | 3.39 | 2.72 | 0.12 | 3.10 | 2.69 |
| B | 0.13 | 3.42 | 2.71 | 0.12 | 3.47 | 2.81 | 0.15 | 3.31 | 2.90 |
| C | 0.13 | 3.45 | 2.73 | 0.13 | 3.46 | 2.83 | 0.15 | 3.33 | 2.93 |

It can be seen from these results that Comparative Sample A undergoes serious deterioration of γ and Dmax in the case of using the color developing solution which does not contain benzyl alcohol; CD-2, while Samples B and C of the present invention exhibit excellent color formation even if CD-2 is used.

UV-1, UV-2 and UV-3 in Table 2 are compounds having the following structure.

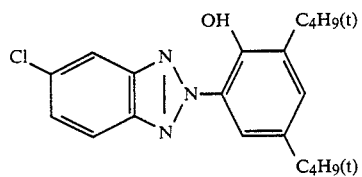

UV - 1:

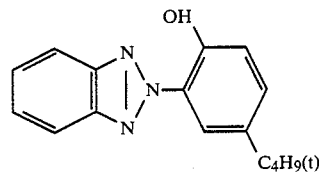

UV - 2:

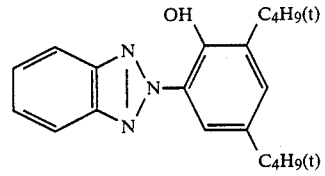

UV - 3:

The amount of couplers of the present invention used in color light-sensitive materials and other constructions in the color light-sensitive materials of the present invention are described below.

The amount of couplers of the present invention and other couplers is not restricted, but preferably is in a range of $2 \times 10^{-3}$ mols to $5 \times 10^{-1}$ mols, preferably $1 \times 10^{-2}$ mols to $5 \times 10^{-1}$ mols, per mol of silver in the silver halide emulsion layer.

In order to introduce the couplers into silver halide emulsion layers, known processes, for example, a process described in U.S. Pat. No. 2,322,027, etc. can be used. For example, after the couplers are dissolved in phthalic acid alkyl esters (for example, dibutyl phthalate and dioctyl phthalate, etc.), phosphoric acid esters (for example, diphenyl phosphate, triphenyl phosphate, tricresyl phosphate and dioctylbutyl phosphate), citric acid esters (for example, tributyl acetylcitrate), benzoic acid esters (for example, octyl benzoate), alkylamides (for example, diethyllaurylamide), aliphatic acid esters (for example, dibutoxyethyl succinate) for trimesic acid esters, or organic solvents having a boiling point of about 30° to 150° C., for example, lower alkyl acetates such as ethyl acetate or butyl acetate, ethyl propionate, secondary butyl alcohol, methyl isobutyl ketone, β-ethoxyethyl acetate and methyl cellosolve acetate, etc., they are dispersed in hydrophilic colloids. The above described high boiling point organic solvents and the low boiling point organic solvents may be used as a mixture thereof if desired.

Known ring-opened ketomethylene type couplers can be used as yellow couplers. Among others, benzoylacetanilide type compounds and pivaloylacetanilide type compounds can be advantageously used. Examples of yellow couplers capable of being used include those described in U.S. Pat. Nos. 2,875,057, 3,265,506, 3,408,194, 3,551,155, 3,582,322, 3,725,072 and 3,891,445, German Pat. No. 1,547,868, German Patent Application Nos. (OLS) 2,219,917, 2,261,361 and 2,414,006, British Pat. No. 1,425,020, Japanese Patent Publication No. 10783/76 and Japanese Patent Application (OPI) Nos. 26133/72, 73147/73, 102636/76, 6341/75, 123342/75, 130442/75, 21827/76, 87650/75, 82424/77 and 115219/77, etc.

Pyrazolone type compounds, imidazolone type compounds and cyanoacetyl type compounds, etc., can be used as magenta couplers. Particularly, pyrazolone type compounds can be advantageously used. Examples of magenta couplers capable of being used include those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German Patent Application (OLS) Nos. 2,408,665, 2,417,945, 2,418,959 and 2,424,467, Japanese Patent Publication No. 6031/65 and Japanese Patent Application (OPI) Nos. 20826/76, 58922/77, 129538/74, 74027/74, 159336/75, 42121/77, 74028/74, 60233/75, 26541/76 and 55122/78, etc.

Phenol type compounds and naphthol type compounds, etc. can be used as cyan couplers. Examples of these couplers include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329 and Japanese Patent Application (OPI) Nos. 59838/73, 26034/76, 5055/73, 146828/76, 69624/77 and 90932/77.

It is possible to use, for example, those described in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and German Patent Application (OLS) Nos. 2,418,959 as colored couplers.

It is possible to use, for example, those described in U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454, Japanese Patent Application (OPI) Nos. 69624/77 and 122335/74 and Japanese Patent Publication No. 15141/76 as development inhibitor releasing (DIR) couplers.

The light-sensitive materials used in the present invention may contain compounds which release a development inhibitor on development, other than DIR couplers. For example, it is possible to use those described in U.S. Pat. Nos. 3,297,445 and 3,379,529, German Patent Application (OLS) No. 2,417,914 and Japanese Patent Application (OPI) Nos. 15271/77 and 9116/78.

Two or more of the above described couplers may be present in the same layer if desired. The same compound also may be present in two or more different layers if desired. These couplers are generally employed in an amount of $2 \times 10^{-3}$ mols to $5 \times 10^{-1}$ mols, preferably, $1 \times 10^{-2}$ mols to $5 \times 10^{-1}$ mols, per mol of silver in the emulsion layer.

Hydrophilic colloid layers used in the light-sensitive materials produced according to the present invention may contain ultraviolet ray absorbing agents. For example, it is possible to use benzotriazole compounds substituted with aryl groups (for example, those described in U.S. Pat. No. 3,533,794), 4-thiazolidone compounds (for example, those described in U.S. Pat. Nos. 3,314,794 and 3,352,681), benzophenone compounds (for example, those described in Japanese Patent Application (OPI) No. 2784/71), cinnamic acid ester compounds (for example, those described in U.S. Pat. Nos. 3,705,805 and 3,707,375), butadiene compounds (for example, U.S. Pat. No. 4,045,229) and benzoxazole compounds. Further, compounds described in U.S. Pat. No. 3,499,762 and Japanese Patent Application (OPI) No. 48535/79 can be employed. Ultraviolet ray absorbing couplers (for example, α-naphthol type cyan dye forming couplers) or ultraviolet ray absorbing polymers, etc. may be used, too. These ultraviolet ray absorbing agents may be mordanted in a specified layer if desired.

The photographic emulsions used in the present invention can be prepared according to processes described in P. Glarfkides, *Chimie et Physique Photographique*, (published by Paul Montel Co., 1977), G. F. Duffin, *Photographic Emulsion Chemistry*, (published by the Focal Press, 1966) and V. L. Zelikman et al, *Making and Coating Photographic Emulsions*, (published by the Focal Press, 1964), etc. Namely, any acid processes, neutral processes and ammonia processes may be used. Further, as the type of reaction of soluble silver salts with soluble halogen salts, any of one-side mixing processes, simultaneous mixing processes and combinations thereof may be used.

It is also possible to use a process wherein grains are formed in the presence of excess silver ions (the so-called back-mixing process). As a type of the simultaneous mixing process, it is possible to use a process wherein the liquid phase of forming silver halide is kept at a constant pAg, namely, the so-called controlled double jet process, too. According to this process, silver halide emulsions having a regular crystal form and a nearly uniform particle size are obtained.

Two or more silver halide emulsions produced respectively may be used as a mixture, if desired.

Formation of silver halide grains or physical ageing may be carried out in a presence of cadmium salts, zinc salts, lead salts, thallium salts, iridium salts or complex salts thereof, rhodium salts or complex salts thereof, and iron salts or complex salts thereof, etc.

Gelatin is advantageously used as binders or protective colloids for photographic emulsions, but other hydrophilic colloids can be used, too.

For example, it is possible to use proteins such as gelatin derivatives, graft polymers of gelatin and other high polymers, albumin or casein, etc., saccharose derivatives such as cellulose derivatives such as hydroxyethyl cellulose, carboxymethyl cellulose or cellulose sulfate, etc., sodium alginate or starch derivatives, etc., and synthetic hydrophilic high molecular weight substances such as homo- or copolymers, e.g., as polyvinyl alcohol, polyvinyl alcohol partial acetal, poly-N-vinyl pyrrolidone, polyacrylic acid, polymethacrylic acid, polyacrylamide, polyvinyl imidazole or polyvinyl pyrazole, etc.

As gelatin, not only lime processed gelatin but also acid treated gelatin and enzyme treated gelatin described in *Bull. Soc. Sci. Phot. Japan:* No. 16, page 30 (1966) may be used. Further, hydrolyzed products or enzymatic decomposition products of gelatin can be used, too. Suitable gelatin derivatives which can be used include those obtained by reacting gelatin with various compounds such as acid halides, acid anhydrides, isocyanates, bromoacetic acid, alkanesultones, vinylsulfonamides, maleinimide compounds, polyalkylene oxides or epoxy compounds, etc. Examples of these compounds are described in U.S. Pat. Nos. 2,614,928, 3,132,945, 3,186,846 and 3,312,553, British Pat. Nos. 861,414, 1,033,189 and 1,005,784, and Japanese Patent Publishing No. 26845/67, etc.

As the above described gelatin-graft polymers, it is possible to use those which are prepared by grafting homo- or copolypers of vinyl monomers such as acrylic acid, methacrylic acid, derivatives thereof such as esters or amides, etc., acrylonitrile or styrene, etc., on gelatin. Particularly, it is preferred to use graft polymers composed of gelatin and polymers having a some degree of compatibility with gelatin, for example, polymers of acrylic acid, methacrylic acid, acrylamide, methacrylamide or hydroxyalkyl methacrylate, etc. Examples of such compounds are described in U.S. Pat. Nos. 2,763,625, 2,831,767 and 2,956,884, etc.

Typical synthetic high molecular weight substances are those described in, for example, German Patent Application (OLS) No. 2,312,708, U.S. Pat. Nos. 3,620,751 and 3,879,205 and Japanese Patent Publication No. 7561/68.

In order to prevent fogging in the process for producing light-sensitive materials, during storage or during photographic processings or to stabilize photographic properties, various compounds can be incorporated in the photographic emulsions in the present invention. For example, it is possible to add various compounds known as antifogging agents or stabilizers, such as thiazoles, for example, benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles and mercaptotetrazoles (particularly, 1-phenyl-5-mercaptotetrazole), etc.; mercaptopyrimidines; mercaptotriazines; thioketo compounds such as oxazolinethione; azaindenes, for example, triazaindenes, tetrazaindenes (particularly, 4-hydroxyl substituted (1,3,3a,7)tetrazaindenes) and pentazaindenes, etc.; benzenethiosulfonic acid, benzenesulfinic acid or benzenesulfonamide, etc. For example, it is possible to use the compounds described in U.S. Pat. Nos. 3,954,474 and 3,982,947 and Japanese Patent Publication No. 28660/77.

The photographic emulsion layers in photographic light-sensitive materials of the present invention may contain polyalkylene oxides or derivatives thereof such as the ethers, esters or amines thereof, etc., thioether compounds, thiomorpholines, quatenary ammonium salt compounds, urethane derivatives, urea derivatives, imidazole derivatives and 3-pyrazolidones, etc., for the purpose of increasing sensitivity, improving contrast or accelerating development. For example, it is possible to use those compounds described in U.S. Pat. Nos. 2,400,532, 2,423,549, 2,716,062, 3,617,280, 3,772,021 and 3,808,003 and British Pat. No. 1,488,991, etc.

The photographic emulsions used in the present invention may be spectrally sensitized with methine dyes or other dyes. Examples of dyes which can be used include cyanine dyes, merocyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes and complex merocyanine dyes. In these dyes, it is possible to have any nucleus conventionally used for cyanine dyes as the basic heterocyclic nucleus. Namely, it is possible to have a pyrroline nucleus, oxazoline nucleus, thiazoline nucleus, pyrrole nucleus, oxazole nucleus, thiazole nucleus, selenazole nucleus, imidazole nucleus, tetrazole nucleus and pyridine nucleus, etc.; the above described nuclei to which an alicyclic hydrocarbon ring is fused; and the above described nuclei to which an aromatic hydrocarbon ring is fused, namely, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus, etc. These nuclei may have substituents on the carbon atoms thereof.

In merocyanine dyes and complex merocyanine dyes, 5- or 6-member heterocyclic nuclei such as a pyrazolin-5-one nucleus, a thiohydantoin nucleus, a 2-thioxazolidine-2,4-dione nucleus, a thiazoline-2,4-dione nucleus, a rhodanine nucleus or a thiobarbituric acid nucleus, etc., may be present as nuclei having a ketomethylene structure.

Examples of suitable sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588 and Japanese Patent Publications Nos. 14030/69 and 24847/77.

These sensitizing dyes may be used alone, or combinations of them can be used if desired. Combinations of sensitizing dyes are used frequently for the purpose of, particularly, supersensitization. Examples of such have been described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publications Nos. 4936/68 and 12375/78 and Japanese Patent Applications (OPI) Nos. 110618/77 and 109925/77, etc.

The emulsions may contain dyes which do not have a spectral sensitization function themselves or substances which do not substantially absorb visible light but exhibit supersensitization together with the sensitizing dyes. For example, they may contain aminostyryl compounds (for example, those described in U.S. Pat. Nos. 2,933,390 and 3,635,721), aromatic organic acid-formaldehyde condensation products (for example, those described in U.S. Pat. No. 3,743,510), cadmium salts and azaindene compounds, etc. Combinations described in U.S. Pat. Nos. 3,615,613, 3,615,641, 3,617,295 and 3,635,721 are particularly useful.

In the light-sensitive materials produced according to the present invention, the hydrophilic colloid layers may contain water soluble dyes as filter dyes or for the purpose of anti-irradiation and for other purposes. Examples of such dyes include oxonol dyes, hemioxonol dyes, styryl dyes, merocyanine dyes, cyanine dyes and azo dyes. Of these, oxonol dyes, hemioxonol dyes and merocyanine dyes are especially useful Examples of dyes which can be used include those described in British Pat. Nos. 584,609 and 1,177,429, Japanese Patent Publications (OPI) Nos. 85130/73, 99620/74, 114420/74 and 108115/77 and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

In the light-sensitive materials produced according to the present invention, the photographic emulsion layers and other hydrophilic colloid layers may contain whitening agents such as stilbene type, triazine type, oxazole type or coumarine type whitening agents. They may be water-soluble, and water-insoluble whitening agents may be used in the form of a dispersion.

Examples of suitable fluorescent whitening agents are described in U.S. Pat. Nos. 2,632,701, 3,169,840 and 3,359,102 and British Pat. Nos. 852,075 and 1,319,763, etc.

In practicing the present invention, the following known anti-fogging agents can be used alone. Further, color image stabilizers which can be used in the present invention may be used alone or as a combination of two or more of them. Examples of known anti-fading agents include hydroquinone derivatives described in U.S. Pat. Nos. 2,360,290, 2,418,613, 2,675,314, 2,701,197, 2,704,713, 2,728,659, 2,732,300, 2,735,765, 2,710,801 and 2,816,028, and British Pat. No. 1,363,921, etc., gallic acid derivatives described in U.S. Pat. Nos. 3,457,079 and 3,069,262, etc., p-alkoxyphenols described in U.S. Pat. Nos. 2,735,765 and 3,698,909 and Japanese Patent Publications Nos. 20977/74 and 6623/77, p-oxyphenol derivatives described in U.S. Pat. Nos. 3,432,300, 3,573,050, 3,574,627 and 3,764,337 and Japanese Patent Applications (OPI) Nos. 35633/77, 147434/77 and 152225/77, and bisphenols described in U.S. Pat. No. 3,700,455, etc.

The light-sensitive materials produced according to the present invention may contain hydroquinone derivatives, aminophenol derivatives, gallic acid derivatives and ascorbic acid derivatives, etc., as anti-color-fogging agents. Examples of such are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Applications (OPI) Nos. 92988/75, 92989/75, 93928/75, 110337/75 and 146235/77 and Japanese Patent Publication No. 23813/75.

The present invention can be employed in multilayer multicolor photographic materials having at least two layers each with a different spectral sensitivity, on a support. Multilayer natural color photographic materials generally have at least a red-sensitive silver halide emulsion layer, at least a green-sensitive silver halide emulsion layer and at least a blue-sensitive silver halide emulsion layer on a base. The order of these layers is suitably selected as needed. In general, the red-sensitive emulsion layer contains a cyan coupler, the green-sensitive emulsion layer contains a magenta coupler, and the blue-sensitive emulsion layer contains a yellow coupler, but, if desired, other combinations can be utilized.

In order to carry out photographic processing of the light-sensitive materials of the present invention, any known process can be used and known processing solutions can be used also. Further, the processing temperature can be selected from a range of 18° C. to 50° C. in general, but a temperature lower than 18° C. or a temperature higher than 50° C. can be used, if desired. It is possible to utilize any development processing for forming silver images (black-white photographic processing) and color photographic processing comprising development for forming dye images, according to the purpose.

The color developing solution employed is generally composed of an alkaline aqueous solution containing a color developing agent. Suitable color developing agents which can be used include known primary aromatic amine developing agents, for example, phenylenediamines (for example, 4-amino-N,N-diethylaniline, 3-methyl-4-amino-N,N-diethylaniline, 4-aminoethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline and 4-amino-3-methyl-N-ethyl-N-β-methoxyethylaniline, etc.).

In addition, the compounds described in L. F. A. Mason, *Photographic Processing Chemistry*, pages 226–229 (published by Focal Press, 1966), U.S. Pat. Nos. 2,193,015 and 2,592,364 and Japanese Patent Application (OPI) No. 64933/73, etc., may be used.

The color developing solution may contain pH buffer agents such as alkali metal sulfites, carbonates, borates or phosphates, and development restrainers or antifogging agents such as bromides, iodides or organic antifoggants, etc. Further, the developing solution may contain, as the occasion demands, water softeners, preservatives such as hydroxylamine, organic solvents such as benzyl alcohol or diethylene glycol, development accelerators such as polyethylene glycol, quaternary ammonium salts or amines, dye forming couplers, competing couplers, fogging agents such as sodium borohydride, auxiliary developing agents such as 1-phenyl-3-pyrazolidone, viscosity increasing agents, polycarboxylic acid type chelating agents described in U.S. Pat. No. 4,083,723, and antioxidants described in German Patent Application (OLS) No. 2,622,950, etc.

The photographic emulsion layers after color development are generally subjected to bleaching processing. The bleaching processing may be carried out simultaneously with the fixing processing or may be carried out separately. Suitable bleaching agents include compounds of polyvalent metals such as iron (III), cobalt (III), chromium (VI) or copper (II), etc., peracids, quinones and nitroso compounds, etc. For example, it is possible to use ferricyanides, bichromates, organic complex salts of iron (III) or cobalt (III), for example, complex salts of aminopolycarboxylic acids such as ethylenediaminetetraacetic acid, nitrilotriacetic acid or 1,3-diamino-2-propanol-tetraacetic acid, etc., or organic acids such as citric acid, tartaric acid or malic acid, etc.; persulfates, permanganates; and nitrosophenol, etc. Of these, potassium ferricyanide, sodium ethylenediaminetetraacetato iron (III) complex and ammonium ethylenediaminetetraacetato iron (III) complex are particularly useful. Ethylenediaminetetraacetato iron (III) complex salts are available in both bleaching solution and one-bath bleach-fixing solution, and it is possible to add various additives such as bleaching accelerators described in U.S. Pat. Nos. 3,042,520 and 3,241,966 and Japanese Patent Publications Nos. 8506/70 and 8836/70, etc., thiol compounds described in Japanese Patent Application (OPI) No. 65732/78, and other compounds.

While the invention has been described in detail and with reference to specific embodimens thereof, it will be apparent to one skilled in the art that various changes and modifications can be made therein without departing from the spirit and scope thereof.

What is claimed is:

1. A silver halide color photographic light-sensitive material containing a coupler having at least one of a sulfamoylphenylenesulfonyl group, a sulfamoylaminophenylenesulfonyl group and a sulfonamidophenylenesulfonyl group as a substituent.

2. The light-sensitive material of claim 1, wherein said coupler is represented by the following general formula

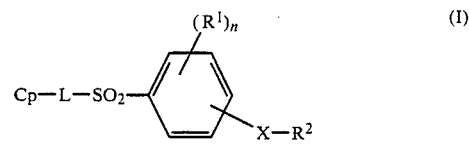

where Cp represents a coupler residue, L represents a divalent linking group and X represents $-NHSO_2-$,

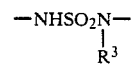

or $-SO_2NH-$; and n represents 0–4, $R^1$ represents a substituent on the benzene ring, $R^2$ represents an alkyl group, an aryl group or an alkoxy group, which may be a hydrogen atom or a hydroxyl group where X is —NHSO₂NR³— or —SO₂NH—, R³ represents a substituent on the nitrogen atom, and is selected from the group consisting of a hydrogen atom, an alkyl group, an aryl group, an alkoxy group, a hydroxyl group or a heterocyclic residue, and R² and R³ may combine and form a ring, and n is 0, 1, 2, 3 or 4.

3. The light-sensitive material of claim 2, wherein Cp represents a cyan coupler residue, a magenta coupler residue or a yellow coupler residue.

4. The light-sensitive material of claim 2, wherein Cp represents a coupler residue for forming a black dye, a gray dye or a coloring compound.

5. The light-sensitive material of claim 2, wherein said coupler is represented by the following general formula (II)

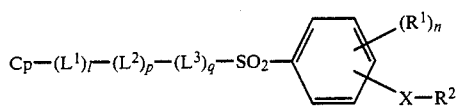

wherein Cp, R¹, R², X and n have each the same meaning as in the general formula (I) in claim 2, and l, p and q each is 0 or 1, L¹ represents a divalent group selected from groups of the formula

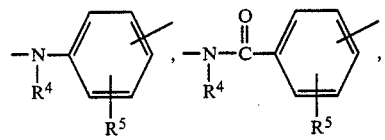

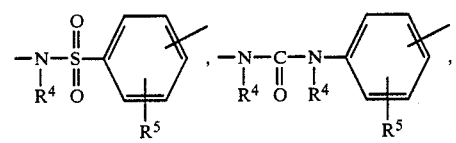

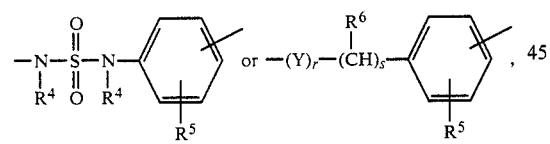

L² represents a divalent group selected from groups of the formula

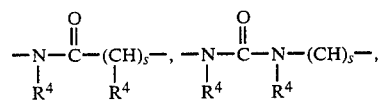

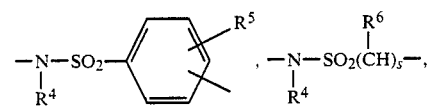

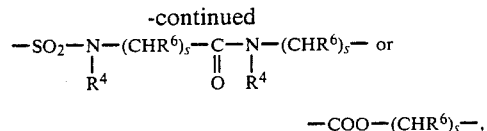

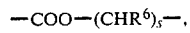

L³ represents a divalent group selected from groups of the formula

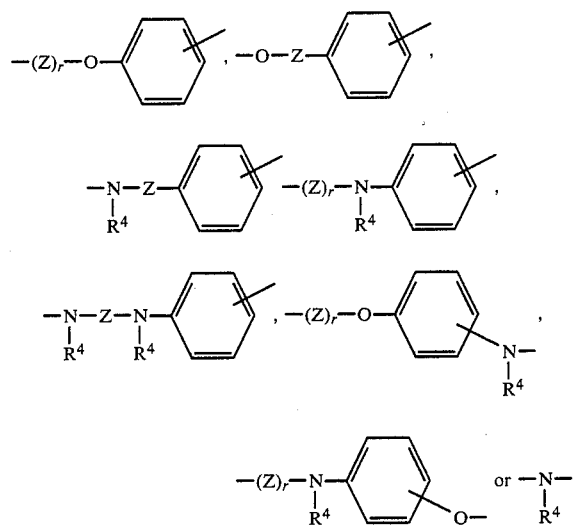

R⁴ and R⁶ represent each a hydrogen atom, an alkyl group or an aryl group, R⁵ represents a hydrogen atom, a halogen atom, an alkyl group, an alkoxy group, a sulfamoyl group, a sulfamoylamino group, a carbonamido group, a carbamoyl group, a sulfonamido group, an acyl group, a ureido group, a carboxyl group, a carbamate group, a cyano group or a nitro group, Y represents —O— or —S—, Z represents —CO— or —SO₂—, r is 0 or 1, and s is 0 to 10.

6. The light-sensitive material of claim 5, wherein said coupler is represented by the following general formulas (III) and (IV):

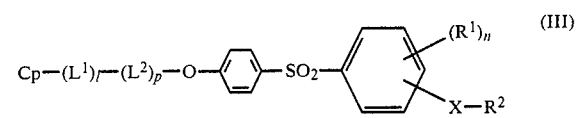

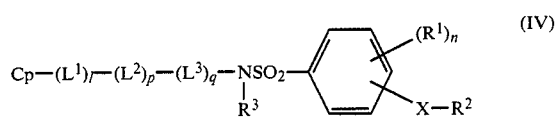

wherein Cp, L¹, L², L³, R¹, R², R³, X, l, p, q and n each have the same meaning as in the general formula (II) of claim 5.

7. The light-sensitive material of claim 1, wherein said coupler is present in an amount of $2 \times 10^{-3}$ to $5 \times 10^{-1}$ moles of coupler per mole of silver in the silver halide emulsion layer.

* * * * *

UNITED STATES PATENT AND TRADEMARK OFFICE
CERTIFICATE OF CORRECTION

PATENT NO. : 4,525,450

DATED : June 25, 1985

INVENTOR(S) : ISAMU ITOH ET AL

It is certified that error appears in the above-identified patent and that said Letters Patent is hereby corrected as shown below:

On the title page the following should be added:

--Assignee: Fuji Photo Film Co., Ltd.--.

Signed and Sealed this

Nineteenth Day of November 1985

[SEAL]

Attest:

DONALD J. QUIGG

Attesting Officer

Commissioner of Patents and Trademarks